(12) United States Patent
Daigh et al.

(10) Patent No.: US 8,513,012 B2
(45) Date of Patent: Aug. 20, 2013

(54) METHOD FOR PRODUCTION OF MAST CELLS FROM STEM CELLS

(75) Inventors: Christine Daigh, Middleton, WI (US); Deepika Rajesh, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 925 days.

(21) Appl. No.: 12/435,123

(22) Filed: May 4, 2009

(65) Prior Publication Data

US 2009/0275131 A1 Nov. 5, 2009

Related U.S. Application Data

(60) Provisional application No. 61/050,086, filed on May 2, 2008.

(51) Int. Cl.
*C12N 5/00* (2006.01)
*C12N 5/02* (2006.01)

(52) U.S. Cl.
USPC .......................................... 435/377; 435/375

(58) Field of Classification Search
None
See application file for complete search history.

(56) References Cited

U.S. PATENT DOCUMENTS

| | | | |
|---|---|---|---|
| 7,449,334 B2 | 11/2008 | Thomson et al. | 435/377 |
| 2007/0077654 A1 | 4/2007 | Thomson et al. | 435/372 |
| 2009/0081784 A1 | 3/2009 | Vodyanyk et al. | 435/372 |

FOREIGN PATENT DOCUMENTS

WO WO 2008/089351 7/2008

OTHER PUBLICATIONS

Baker, M. (2008) Rat embryonic stem cells created. Nature, published online Dec. 24, 2008, doi: 10.1038/news.2008.1336.*
Brevini et al. (2010) No shortcuts to pig embryonic stem cells. Theriogenology 74: 544-550.*
Cao et al. (2009) Isolation and culture of primary bovine embryonic stem cell colonies by a novel method. Journal of Experimental Zoology 311A(5): 368-376.*
Paris et al. (2010) Equine embryos and embryonic stem cells: Defining reliable markers of pluripotency. Theriogenology 74: 516-524.*
Schneider et al. (2010) Canine embryonic stem cells: State of the art. Theriogenology 74(4): 492-497.*
Ludwig et al. (2006) Derivation of human embryonic stem cells in defined conditions. Nature Biotechnology 24(2): 185-187.*
Definition of "murine" (1996) Merriam-Webster's Collegiate Dictionary, tenth edition, Springfield, MA: Merriam-Webster, Inc., p. 766.*
Ma et al. (Nov. 2007) Direct development of functionally mature tryptase/chymase double-positive connective tissue-type mast cells from primate embryonic stem cells. Stem Cells 26: 706-714.*
Purpura et al. (Sep. 2008) Analysis of the temporal and concentration-dependent effects of BMP-4, VEGF, and TPO on development of embryonic stem cell-derived mesoderm and blood progenitors in a defined, serum-free media. Experimental Hematology 36: 1186-1198.*
Sawai et al. (1999) Thrombopoietin augments stem cell factor-dependent growth of human mast cells from bone marrow multipotential hematopoietic progenitors. Blood 93(11): 3703-3712.*
Willheim et al. (1995) Purification of human basophils and mast cells by multistep separation technique and mAb to CDw17 and CD117/c-kit. Journal of Immunological Methods 182: 115-129.*
Chang et al., "From hematopoietic stem cells to platelets," *Journal of Thrombosis and Haemostasis*, 5(Suppl 1):318-327, 2007.
Okayama et al., "Development migration, survival of mast cells," *Immunologic Research*, 34(2):97-115, 2006.
PCT International Search Report and Written Opinion, issued in International application No. PCT/US2009/042701, mail date Aug. 5, 2009.
Pick et al., "Differentiation of human embryonic stem cells in serum-free medium reveals distinct roles for bone morphogenetic protein 4, vascular endothelial growth factor, stem cell growth, an fibroblast growth factor 2 in hematopoiesis," *Stem Cells*, 25(9):2206-2214, 2007.
Tian, "Hematopoietic development of human embryonic stem cells in culture," *Methods in Molecular Biology*, 430:119-133, 2008.
Vodyanik et al., "Hematoendothelial differentiation of human embryonic stem cells," *Current Protocols in Cell Biology*, Juan S. Bonifacino et al., Eds., Chap. 23, page unit 23.6, 2007.
Conti et al., "Role of mast cells in tumor growth," *Ann. Clin. Lab. Sci.*, 37(4):315-322, 2007.
Gaur et al., "Megakaryocytes derived from human embryonic stems cells: a genetically tractable system to study megakaryocytopoiesis and integrin function," *J. Thromb. Haemost.*, 4(2):436-42, 2006.
Huangfu et al. "Induction of pluripotent stem cells from primary human fibroblasts with only Oct4 and Sox2," *Nat Biotechnol.* 26(11):1269-75, 2008.
Jensen et al., "Concurrent inhibition of kit- and FcepsilonRI-mediated signaling: coordinated suppression of mast cell activation," *J Pharmacol Exp Ther.* 324(1):128-38, 2008.
Lappalainen et al., "A protocol for generating high numbers of mature and functional human mast cells from peripheral blood," *Clin. Experim. Allergy*, 37:1404-1414, 2007.
Lu, et al., "Generation of functional hemangioblasts from human embryonic stem cells," *Nature Methods*, 4(6):501-509, 2007.
Ludwig et al., "Derivation of human embryonic stem cells in defined conditions," *Nature Biotech.*, (2):185-187, 2006a.
Ludwig et al., "Feeder-independent culture of human embryonic stem cells," *Nature Methods*, 3(8):637-646, 2006b.
Ma et al., "Novel method for efficient production of multipotential hematopoietic progenitors from human embryonic stem cells," *Int. J. of Hematology*, 85:371-379, 2007.
Nakagawa et al. "Generation of induced pluripotent stem cells without Myc from mouse and human fibroblasts," *Nat. Biotechnol.*, 26(1):101-106, 2008.
Ochi et al., "T helper cell type 2 cytokine-mediated comitogenic responses and CCR3 expression during differentiation of human mast cells in vitro," *J. Exp. Med.*, 190:267-280, 1999.

(Continued)

*Primary Examiner* — Anne-Marie Falk
(74) *Attorney, Agent, or Firm* — Parker Highlander PLLC

(57) ABSTRACT

Provided are methods for generating mast cells from pluripotent stem cells in vitro. Methods are disclosed for the differentiation of pluripotent cells, such as iPS cells and/or human embryonic stem cells, into mast cells. The resulting mast cells may be used for various purposes including screening cells for drug development and research. Growth factors which may be included in culture media according to the present invention include stem cell factor (SCF), FLT-3 ligand, thrombopoietin (TPO), interleukin-3 (IL-3), and/or interleukin-6 (IL-6).

23 Claims, 5 Drawing Sheets

(56) References Cited

OTHER PUBLICATIONS

Saito et al., "Selective growtn of human mast cells induced by stell factor, IL-6, and prostagiandin E2 from cord blood mononuclear cells," *J. Immunol.*, 157:343-350, 1996.

Schernthaner et al., "Expression, epitope analysis, and functional role of the LFA-2 antigen detectable on neoplastic mast cells," *Blood*, 98:3784-3792, 2001.

Valent et al., "Induction of differentiation of human mast cells from bone marrow and peripheral blood mononuclear cells by recombinant human stem cell factor/kit-ligand in long-term culture," *Blood*, 80:2237-2245, 1992.

Wang et al., "Buffy coat preparation is a convenient source of progenitors for culturing mature human mast cells," *J. Immunol. Methods*, 309:69-74, 2006.

Zhou et al. "Generation of induced pluripotent stem cells using recombinant proteins," *Cell Stem Cell*, (2009) doi:10.1016/jstem.2009.04.005.

Chung et al., "Human embryonic stem cell lines generated without embryo destruction," *Cell Stem Cell*, 2:113-117, 2008.

Office Action issued in European Application No. 09 740 008.9, mailed Oct. 15, 2012.

\* cited by examiner

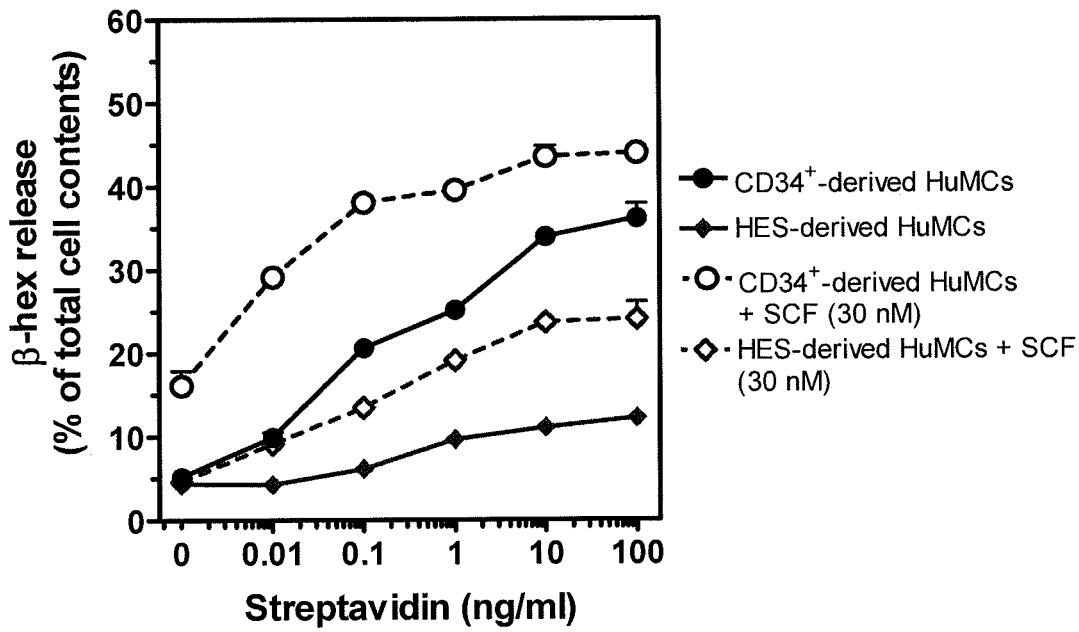
FIG. 1A: CD34+- and HES-derived HuMCs Streptavidin+/-SCF
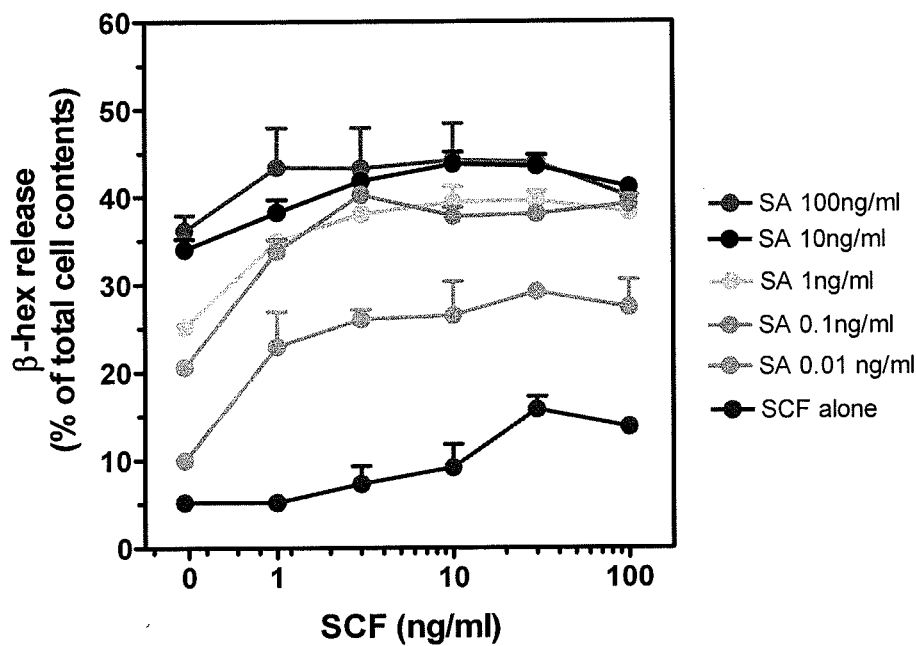
FIG. 1B: CD34+-derived HuMCs Streptavidin+SCF

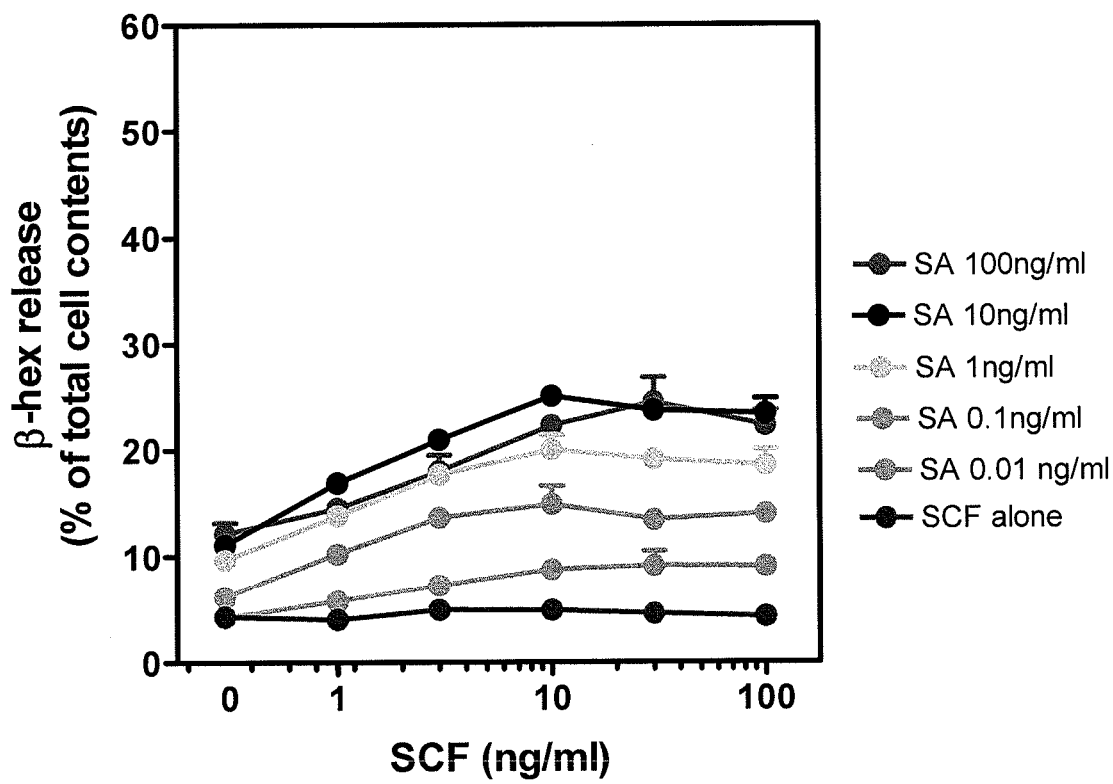
FIG. 1C: HES-derived HuMCs Streptavidin+SCF
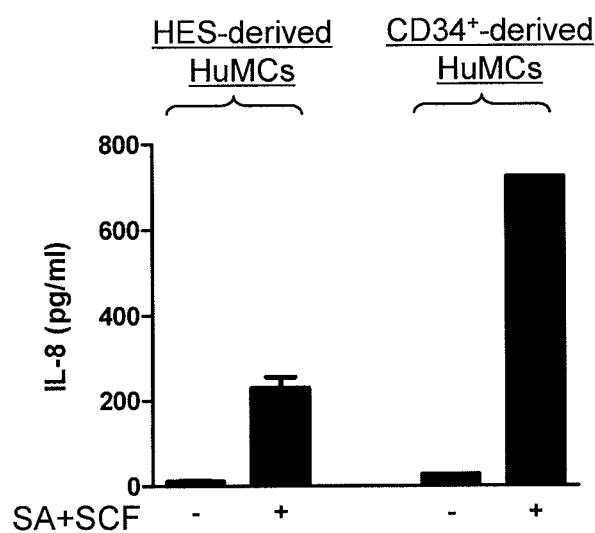
FIG. 2A: IL-8 Cytokine Release

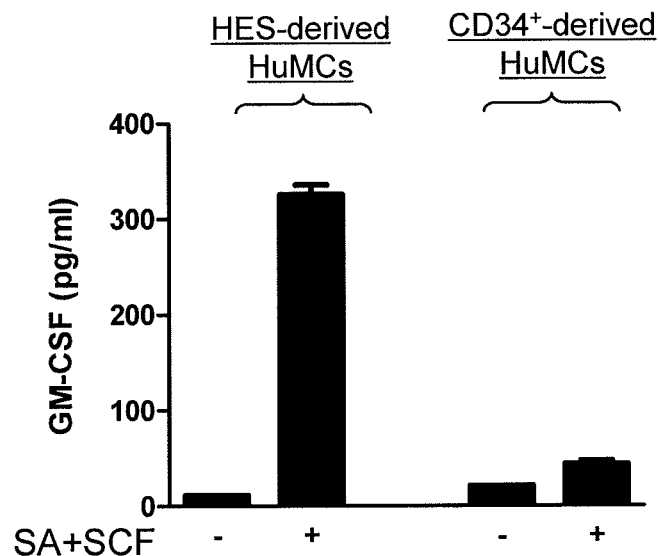
FIG. 2B: GM-CSF Cytokine Release
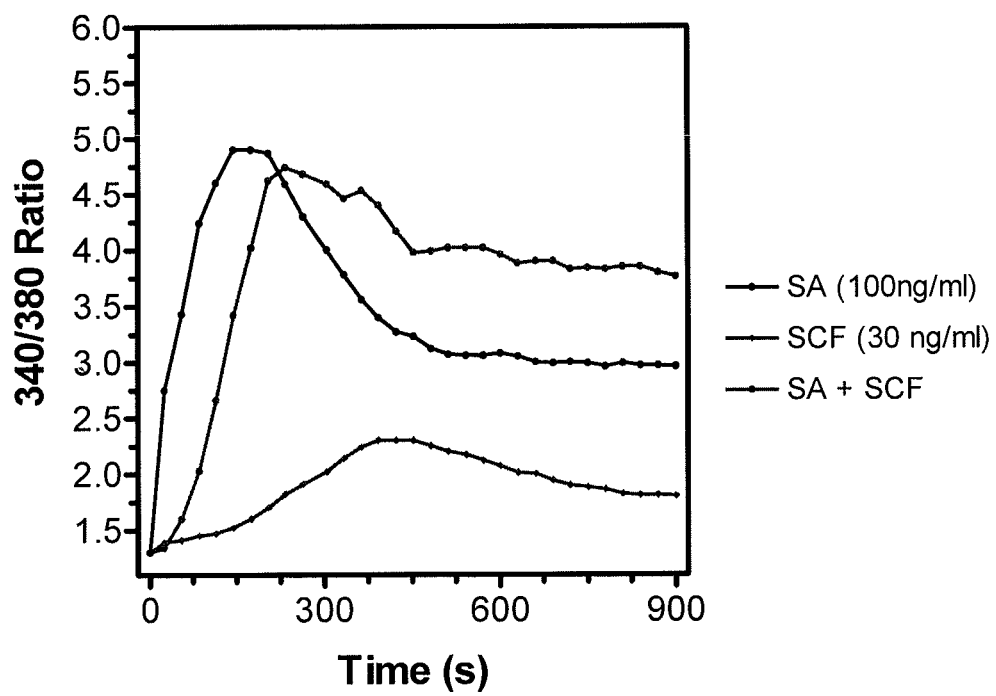
FIG. 3A: CD34⁺-Derived HuMCs

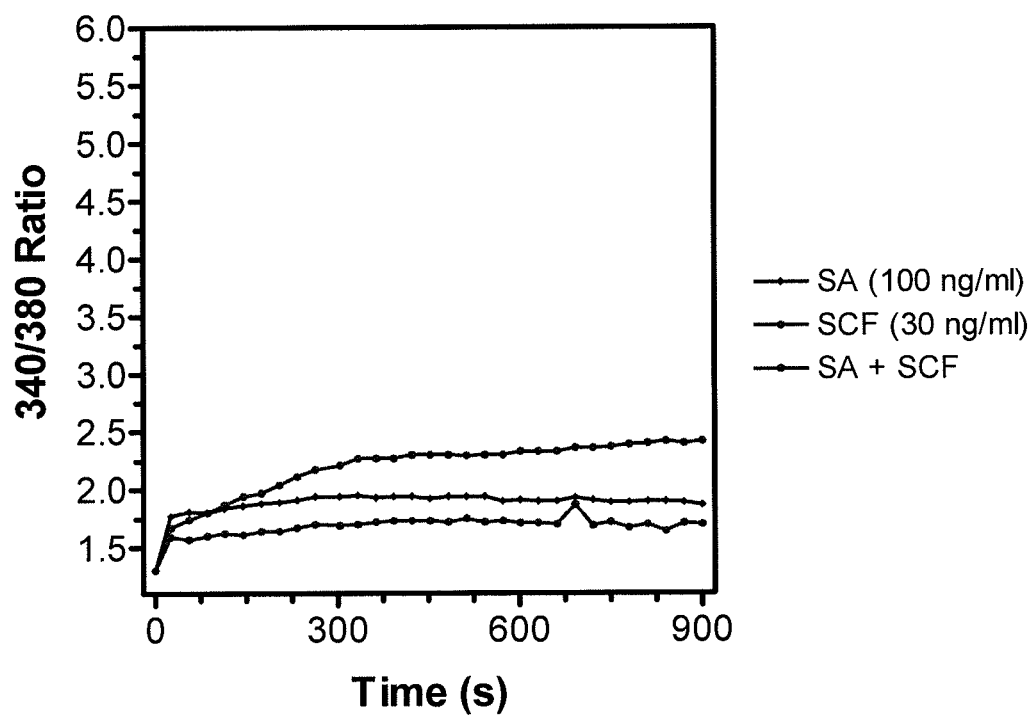

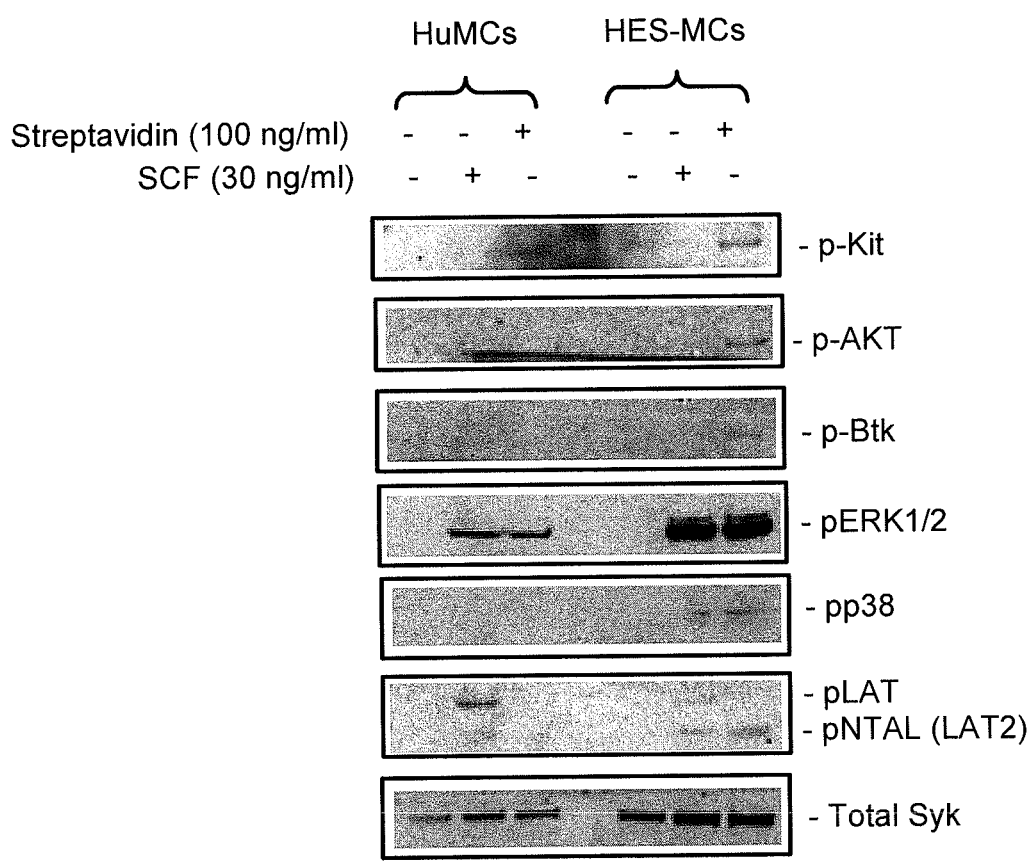

METHOD FOR PRODUCTION OF MAST CELLS FROM STEM CELLS

This application claims priority to U.S. Provisional Application No. 61/050,086 filed on May 2, 2008, the entire disclosure of which is specifically incorporated herein by reference in its entirety without disclaimer.

BACKGROUND OF THE INVENTION

1. Field of the Invention

The present invention relates generally to the fields of molecular biology. More particularly, it concerns methods for the culture and production of mast cells from pluripotent cells.

2. Description of Related Art

Mast cells are cells found in mucosal and connective tissues throughout the body. Mast cells contain many granules rich in histamine and heparin and play a critical role in allergic responses. Mast cells are also involved in protective functions such as wound healing and defense against pathogens. Mature mast cells express high affinity receptors (FcεR1) which can bind IgE monomers. Antigen binding to this IgE triggers mast-cell degranulation and mast cell activation, producing a local or systemic immediate hypersensitivity reaction.

Mast cells can participate in certain inflammatory diseases and cancers. For example, mast cells can secrete proinflammatory cytokines involved in neuro-inflammatory processes and cancer. Mast cells can also accumulate in the stroma surrounding certain tumors such as adenocarcinoma, secreting molecules that can benefit tumors (Conti et al., 2007).

Isolation of mast cells is difficult due to the relatively low abundance and distribution of mast cells in a wide variety of tissues. Because of the difficulty in obtaining human mast cells in sufficient number and with high purity, previous studies largely relied on using rodent mast cells such as rat peritoneal mast cells or mouse bone marrow-derived cultured mast cells; however, rodent cells are not ideal because mast cells are heterogeneous, and there are many differences between species.

Nonetheless, mast cells are economically valuable and important tools for research. Mast cells may be used to test drug toxicity, histamine or granule release responses, and immunology-related responses, such as allergy-related or immune-related responses to compounds. Mast cells can be useful for purposes including drug screening and pre-clinical testing of putative biologically active compounds, including both allergy medicines, such as antihistamines, and non-allergy compounds. A convenient source of mast cells would also be particularly useful for labs interested in researching the biology, structure, and/or function of mast cells.

Previously, mast cells have been cultured from multipotent hematopoietic cord blood cells. Schernthaner et al. (2001) presents data regarding expression of the CD2 antigen by neoplastic cells. In order to analyze the expression of CD2 on immature "nonneoplastic" mast cells, Schernthaner et al. cultures mast cells from CD34+ cord blood cells using a cell culture medium comprising stem cell factor and IL-6. Similarly, Lappalainen et al. (2007) produced mast cells from human peripheral blood-derived CD34+ cells by culturing the multipotent hematopoietic cells in stem cell factor and certain cytokines at various timepoints. Like Schernthaner et al., multipotent hematopoietic progenitor cells were used.

It is currently not clear whether or how approaches using multipotent cells might be used or incorporated into a method for culturing mast cells from other cell types, such as pluripotent cells. In particular, the biological profile of multipotent hematopoietic (CD34+) progenitor cells are distinct from pluripotent cells, and there exists a need for methods for differentiating mast cells from pluripotent cells. In contrast to pluripotent cells, cord blood and other hematopoietic progenitor cells have limited expandability. Thus, for example, additional amounts of cord blood would be needed for the continued production of mast cells. In contrast, the expandability of pluripotent cells or cell lines is theoretically endless.

Differentiation of stem cells into various cell lines is an unpredictable art, and multiple factors including how stem cells are produced and maintained can affect subsequent attempts to differentiate the cells. For example, the responses of pluripotent cells as compared to other cell types, such as cord blood, can vary widely. Multiple factors can even affect the generation of mast cells from multipotent cells. For example, the source of progenitor cells, the methodology used, the number of mast cells generated, the degree of their maturity, and their phenotype and responsiveness towards various stimuli vary greatly (Kambe et al., 2000; Dahl et al., 2002; Wang et al., 2006). Thus, there exists a clear need for methods for the culture and differentiation of pluripotent cells into mast cells, and such methods would beneficially facilitate studies in these areas of research.

SUMMARY OF THE INVENTION

The present invention overcomes limitations in the prior art by providing methods for differentiating pluripotent cells (e.g., human embryonic stem "hESC" cells, human iPS cells) into mast cells. These methods allow the production of mast cells from a cell source (i.e., pluripotent cells) which can be maintained in an undifferentiated state and provide, at least in principle, an almost indefinite source of cells. Thus, in certain embodiments and as stated above, these approaches provide considerable advantages over previous protocols which utilize multipotent cells and may require the repeated collection cells, such as peripheral blood or cord blood, for the generation of mast cells.

In certain aspects, pluripotent cells may be cultured under conditions to induce differentiation into hematopoietic progenitors or hematopoietic stem cells (e.g., culture on mouse embryonic fibroblasts or OP9 cells). The resulting cells may next be cultured under conditions to promote differentiation into megakaryocytes and mast cell precursors. The resulting precursors may be cultured under conditions to promote further differentiation into mast cells (e.g., culturing in a media comprising stem cell factor and IL-6). As shown in the below examples, yields of 90% or more of mast cells may be accomplished via the methods of the present invention. Compositions and differentiation media for accomplishing the foregoing are also provided.

An aspect of the present invention relates to a method of preparing mast cells by culturing pluripotent cells in vitro comprising the steps of: (a) culturing the pluripotent cells under conditions that promote differentiation of the cells into hematopoietic precursors or megakaryocytes, to provide a first cell population comprising hematopoietic precursors or megakaryocytes; and (b) culturing the first cell population under conditions that promote the differentiation into mast cells, to provide a second cell population comprising mast cells; wherein the step (a) culturing step does not employ a co-culture with murine fetal liver-derived stromal cells as a feeder layer. In certain embodiments, the second cell population comprises tryptase-positive mast cells; these mast cells may be tryptase-positive, chymase-negative mast cells or tryptase-positive, chymase-positive mast cells. The pluripotent cells may be human iPS cells or human embryonic stem cells (hESC) (e.g., H1 cells). The pluripotent cells may be maintained on MEFs. In certain embodiments, the pluripotent cells are cultured in a media comprising TPO. The pluripotent cells may be further cultured on mouse embryonic fibroblast feeder cells or OP9 cells. In certain embodiments, the feeder cells are not murine fetal liver-derived stromal cells.

Step (a) may comprise culturing the pluripotent cells under defined conditions. Step (a) may comprise the sequential steps of: (1) culturing or maintaining a plurality of the pluripotent cells in a first defined media comprising at least one growth factor; (2) incubating the cells in a second defined media which is essentially free of BMP4, VEGF, IL3, Flt3 ligand, and GMCSF; (3) culturing the cells in a third defined media comprising an amount of BMP4 and VEGF sufficient to expand or promote differentiation in a plurality of the cells; and (4) culturing the cells in a fourth defined media comprising an amount of IL3, Flt3 ligand, and GMCSF sufficient to expand or promote differentiation in a plurality of the cells; wherein a plurality of the pluripotent cells are differentiated into hematopoietic precursor cells. At least some of the cells are at least partially separated or are substantially individualized prior to step (2). Step 1 preferably carried out at about 20% oxygen; steps (2), (3), and/or (4) may be carried out at about 5-20% oxygen. The cells may be substantially individualized using an enzyme, such as a trypsin or TRYPLE. The cells may be contacted with a ROCK inhibitor and a trypsin inhibitor subsequent to said individualization. In certain embodiments, the ROCK inhibitor is selected from the list consisting of HA-100, H-1152, and Y-27632. In other embodiments, step (a) may comprise differentiating the pluripotent cells into embryoid bodies (EBs). The method may comprise culturing the cells at an atmospheric pressure of about 20%, less than about 20%, about 5%-20%, or about 5% oxygen; in certain embodiments, cell yields may be improved by culturing cells at about 5% oxygen.

Step (a) may comprise culturing the pluripotent cells in a first media comprising at least one, two, three or all of: of FLT-3 ligand, stem cell factor (SCF), thrombopoietin (TPO), interleukin-3 (IL-3), and interleukin-6 (IL-6). In certain embodiments, this culturing step and subsequent differentiating steps may be carried out at about 20% oxygen. The first media may comprise stem cell factor. The FL3, stem cell factor, TPO, IL-3, and IL-6 may be exogenously added and/or recombinant. In certain embodiments, the first media comprises about 10-100 ng/ml FL3, about 10-100 ng/ml stem cell factor, about 10-100 ng/ml TPO, about 10-100 ng/ml IL-3, and about 10-100 ng/ml IL-6 are exogenously added and recombinant.

In certain embodiments, after step (a) a plurality of the pluripotent cells have been differentiated into either megakaryocytes or mast cells, wherein the mast cells are positive for CD117 and CD45, while being negative for CD34. Step (b) may comprise culturing the cells in a media comprising stem cell factor. The media may further comprise interleukin-6 (IL-6). In certain embodiments, the media comprises about 10-100 ng/ml stem cell factor and about 10-100 ng/ml IL-6. The culturing of at least one of step (a) and/or step (b) may be performed using serum-free media. The method may further comprise purifying mast cells using MACS or FACS. In certain embodiments, step (a) comprises culturing cells under conditions which favor differentiation of the pluripotent cells into hematopoietic cells, wherein the resulting hematopoietic cells are cultured under conditions which favor differentiation into mast cells. In certain embodiments, step (a) comprises culturing cells under conditions which favor differentiation of the pluripotent cells into hematopoietic cells and subsequently culturing the hematopoietic cells under conditions which favor differentiation into megakaryocytes, wherein the resulting cells are cultured under conditions which favor differentiation into mast cells.

As used herein, the term "pluripotent cells" includes both stem cells that naturally occur in or are derived from a blastocyst, including various existing hESC cell lines, as well as cells that have been induced to de-differentiate into stem cells or return to a stem-cell-like state (see, e.g., Nakagawa et al., 2008; Yu et al. 2007).

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-C: Degranulation of hESC-derived and CD34+ derived mast cells.

FIGS. 2A-B: Cytokine production of hESC-derived and CD34+ derived mast cells. IL-8 (FIG. 2A), and GM-CSF (FIG. 2B) are shown.

FIGS. 3A-B: Calcium flux in human mast cells (HuMCs). Results are shown for CD34+ derived (FIG. 3A) and hESC-derived (FIG. 3B) mast cells.

FIG. 4: Protein phosphorylation in hESC-derived and CD34+ derived mast cells.

DESCRIPTION OF ILLUSTRATIVE EMBODIMENTS

The present invention provides methods for differentiating pluripotent cells into mast cells. Pluripotent cells are distinct from multipotent cells and include human embryonic stem "ES" cells and human iPS cells. The methods and compositions provided herein allow the production of mast cells from a cell source (i.e., pluripotent cells) which can be maintained in an undifferentiated state and cultured, at least in principle, almost indefinitely. Thus, in certain embodiments and as stated above, these approaches provide considerable advantages over previous protocols using multipotent cells which require the repeated collection of cells, such as peripheral blood or cord blood.

The process for differentiating pluripotent stem cells into mast cells typically begins with the preparation and maintenance of pluripotent stem cells. For example, an existing pluripotent stem cell line may be cultured and maintained in an undifferentiated state using feeder cells, such as mouse embryonic fibroblasts, or the cells may be maintained in an undifferentiated state using a defined media, such as a TeSR media. Alternately, pluripotent cells may be newly obtained for use with the present invention. The pluripotent cells may next be differentiated into hematopoietic progenitors by culture on OP9 stromal cells, e.g., in the presence or absence of supplemented thrombopoietin. After the pluripotent cells have been cultured under conditions to promote differentiation into hematopoietic progenitors (e.g., culture on mouse embryonic fibroblasts or OP9 cells, formation of embryoid bodies, or defined differentiation conditions which may utilize fibronectin, collagen IV, or other matrices), the resulting cells may next be cultured under conditions to promote differentiation into megakaryocytes. Megakaryocyte differentiation may be induced by culturing in a media containing various combinations of growth factors such as FLT-3 ligand, stem cell factor, thrombopoietin, interleukin-3, and interleukin-6. It is envisioned that the step of promoting differentiation into megakaryocytes may be excluded in various embodiments of the present invention (i.e., pluripotent stem cell-derived hematopoietic progenitors may be directly differentiated into mast cells by culture in a mast cell differentiation medium, e.g., containing stem cell factor).

The inventor has made the surprising discovery that the hematopoietic progenitors differentiated from pluripotent stem cells may be then differentiated into mast cells by culture in a media comprising, e.g., stem cell factor, IL-3, and IL-6. As shown in the below examples, yields of 90% or more of mast cells may be accomplished via the methods disclosed herein. These results are surprising given the present uncertainties associated with the culture and differentiation of pluripotent stem cells. Further, these methods provide substantial advantages over previously used methods, e.g., differentiating mast cells from cord blood, due to both the decreased need to obtain additional tissue samples as well as the increased proportion of mast cells produced from the starting cell population. Compositions and differentiation media for accomplishing the foregoing are described below, and various modifications may made to these protocols, as would be appreciated by one of skill.

Interestingly, the inventors have discovered that, when pluripotent cells are cultured on OP9 stromal cells prior to differentiation, "single positive" mast cells (i.e., tryptase positive, chymase negative mast cells) may be produced. Single positive mast cells are distinct from double positive mast cells (i.e., tryptase positive, chymase positive mast cells).

Human mast cells are classified into two phenotypes based on their neutral protease compositions. One is the tryptase-positive and chymase-positive MCTC cell which predominates in the skin and bowel submucosa, and the other is a tryptase-positive and chymasenegative MCT cell predominant in the lung and bowel mucosa. Multiple functional differences exist between both cell types. It has been reported that dispersed mast cells from skin and lung tissues differed in their response to various non-immunologic secretagogues. More specifically, skin mast cells (mainly MCTC) react to compound 48:80 and substance P while lung mast cells (mainly MCT) do not. It has also been demonstrated that MCTC and MCT cells are distinguishable by ultrastructural morphology of their cytoplasmic granules. MCTC cells have granules with incomplete scrolls or crystal-like materials (crystals are much more specific to MCTC), and MCT cells have granules containing particles or discrete scrolls (discrete scrolls are much more specific).

Thus, the generation of single positive mast cells or MCT from hESC or iPS cells may be particularly useful for investigating diseases that involve mast cells present in the lung, including asthma, lung function in chronic obstructive pulmonary disease, angioedema, allergic rhinitis and conjunctivitis, urticaria, and anaphylaxis. The generation of double-positive mast cells or MCTC from hESC or iPS cells may also be particularly useful for investigating diseases which involve histamine release in the skin or bowel submucosa. In various embodiments, the mast cells may be used for the evaluation of an anti-allergy compound; for example, the mast cells may be with an anti-allergy compound and one or more response (e.g., degranulation, etc.) may be measured. Thus, these approaches may be particularly useful for the identification or evaluation of a putative antihistamine, such as a mast cell stabilizer which may inhibit mast cell degranulation or histamine release.

I. PREPARATION AND MAINTENANCE OF PLURIPOTENT STEM CELLS

Embryonic stem cells used with the present invention may be cultured and maintained in an undifferentiated state using a variety of methods, as would be known to one of skill. For example, methods for culturing human embryonic stem cells may utilize either fibroblast feeder cells or a medium which has been exposed to fibroblast feeder cells in order to maintain the stem cells in an undifferentiated state. Pluripotent cells which are differentiated according to the present invention may be first cultured in an undifferentiated state using feeder cells (e.g., mouse embryonic fibroblasts or "MEFs" etc.) or a feeder-independent or defined culture system such as the TeSR medium, e.g., as described in U.S. Application 2006/0084168 and Ludwig et al. (2006a, 2006b).

Feeder-independent culture systems and media may be used to culture and maintain human embryonic stem cells. These approaches allow one to culture and maintain human embryonic stem cells without the need for mouse fibroblast "feeder layers." As described below, various modifications may be made to these methods in order to reduce costs etc. as desired.

As used herein, "pluripotent stem cells" refers to stem cells that have the potential to differentiate into any of the three germ layers: endoderm (e.g., interior stomach lining, gastrointestinal tract, the lungs), mesoderm (e.g., muscle, bone, blood, urogenital), or ectoderm (e.g., epidermal tissues or nervous system). Pluripotent stem cells can differentiate into essentially any fetal or adult cell type, with the exception of extra-embryonic tissues such as placenta. Human embryonic stem cells (hESC) or iPS cells are examples of pluripotent stem cells that may be used with the present invention. In certain embodiments, pluripotent stem cells may be further defined as being non-neoplastic or non-cancerous; nonetheless, the inventors anticipate that certain neoplastic or cancer-derived cell lines such as various teratoma cells or cell lines may be differentiated into mast cells via the methods disclosed herein.

It is anticipated that virtually any human embryonic stem cell line may be used with the present invention, e.g., differentiated into mast cells. For example, human embryonic stem cell line H1, H9, hES2, hES3, hES4, hES5, hES6, BG01, BG02, BG03, HSF1, HSF6, H1, H7, H9, H13B, and/or H14 etc. may be differentiated into mast cells. It is further anticipated that stem cell lines which subsequently become available may also be used with the present invention. Although human embryonic stem cells or human iPS cells are preferably used with the present invention, it is anticipated that other embryonic stem cells, such as mammal, mouse, primate, etc. may be differentiated into mast cells via the methods disclosed herein.

In addition to human embryonic stem cells, induced pluripotent cells, also referred to as iPS cells or iPSC, may be cultured and/or differentiated into mast cells in various embodiments of the present invention. iPS cells are reprogrammed fibroblasts that act like stem cells (Takahashi et al., 2007; Takahashi et al., 2007; Nakagawa et al., 2008; Zhou et al. 2009; US 2009/0081784). iPS cells may be generated via introduction of genetic materials, such as (Oct4, Sox2, Klf4, and c-Myc) or (Oct-4, Sox2, Nanog and Lin28). In certain embodiments, only Oct4 and Sox2 may be used to generate iPS cells from human fibroblasts (Huangfu et al., 2008), and c-Myc may not be required to generate iPS cells (Nakagawa et al., 2008). Alternately, iPS cells may be generated via the exposure to cell penetrating reprogramming proteins as described, e.g., in Zhou et al. 2009, and such iPS cells may also be referred to as "protein-induced pluripotent stem cells" (piPSCs). As used herein, the term "pluripotent stem cells" includes both cells that naturally occur in or are derived from a blastocyst and also cells that have been induced to de-differentiate into stem cells or return to a stem-cell-like state (see, e.g., Nakagawa et al., 2008; Yu et al., 2007; Zhou et al. 2009). iPS cells which may be differentiated into mast cells include, e.g., iPS6.1, iPS 6.6, iPS, iPS 5.6, iPS 5.12, iPS 5.2.15, iPS iPS 5.2.24, iPS 5.2.20, iPS 6.2.1, and/or iPS 5/3-4.3.

A. Approaches Involving TeSR Medium

TeSR medium, also referred to as TeSR1 medium, is a defined medium which may be used to culture undifferentiated human embryonic stem cells. TeSR includes bFGF, LiCl, γ-aminobutyric acid (GABA), pipecolic acid and TGFβ, and various methods utilizing TeSR have been described previously, e.g., in U.S. Application 2006/0084168 and Ludwig et al. (2006a; 2006b), which are incorporated by reference in their entirety without disclaimer.

TeSR medium typically includes inorganic salts, trace minerals, energy substrates, lipids, amino acids, vitamins, growth factors and proteins, and other components. The complete formulation for TeSR1 medium is shown below in Table 2.

TABLE 2

Complete Formulation for TeSR1 Medium

| | mM |
|---|---|
| INORGANIC SALTS | |
| Calcium chloride (Anhydrous) | 8.24E−01 |
| HEPES | 1.18E+01 |
| Lithium Chloride (LiCl) | 9.80E−01 |

TABLE 2-continued

Complete Formulation for TeSR1 Medium

| | mM |
|---|---|
| Magnesium chloride (Anhydrous) | 2.37E−01 |
| Magnesium Sulfate (MgSO4) | 3.19E−01 |
| Potassium chloride (KCl) | 3.26E+00 |
| Sodium bicarbonate (NaHCO3) | 1.80E+01 |
| Sodium chloride (NaCl) | 9.46E+01 |
| Sodium phosphate, dibas (Anhydrous) | 3.92E−01 |
| Sodium phosphate, mono. (NaH2PO4-H2O) | 3.55E−01 |
| TRACE MINERALS | |
| Ferric Nitrate (Fe(NO3)3-9H2O) | 9.71E−05 |
| Ferric sulfate (FeSO4-7H2O) | 1.18E−03 |
| Cupric sulfate (CuSO4-5H2O) | 4.08E−06 |
| Zinc sulfate (ZnSO4-7H2O) | 1.18E−03 |
| Ammonium Metavanadate NH4VO3 | 1.09E−05 |
| Mangenous Sulfate Mn SO4 H2O | 1.97E−06 |
| NiSO4 6H2O | 9.70E−07 |
| Selenium | 1.77E−04 |
| Sodium Meta Silicate Na2SiO3 9H2O | 9.66E−04 |
| SnCl2 | 1.24E−06 |
| Molybdic Acid, Ammonium salt | 1.97E−06 |
| CdCl2 | 1.22E−05 |
| CrCl3 | 1.98E−06 |
| AgNO3 | 9.81E−07 |
| AlCl3 6H2O | 4.87E−06 |
| Ba (C2H3O2)2 | 9.79E−06 |
| CoCl2 6H2O | 9.81E−06 |
| GeO2 | 4.97E−06 |
| KBr | 9.89E−07 |
| KI | 1.00E−06 |
| NaF | 9.83E−05 |
| RbCl | 9.81E−06 |
| ZrOCl2 8H2O | 9.80E−06 |
| ENERGY SUBSTRATES | |
| D-Glucose | 1.37E+01 |
| Sodium Pyruvate | 3.92E−01 |
| LIPIDS | |
| Linoleic Acid | 1.88E−04 |
| Lipoic Acid | 4.00E−04 |
| Arachidonic Acid | 1.29E−05 |
| Cholesterol | 1.12E−03 |
| DL-alpha tocopherol-acetate | 2.90E−04 |
| Linolenic Acid | 6.99E−05 |
| Myristic Acid | 8.59E−05 |
| Oleic Acid | 6.94E−05 |
| Palmitic Acid | 7.65E−05 |
| Palmitoleic acid | 7.71E−05 |
| Stearic Acid | 6.89E−05 |
| AMINO ACIDS | |
| L-Alanine | 1.37E−01 |
| L-Arginine hydrochloride | 5.48E−01 |
| L-Asparagine-H2O | 1.37E−01 |
| L-Aspartic acid | 1.37E−01 |
| L-Cysteine-HCl—H20 | 7.83E−02 |
| L-Cystine 2HCl | 7.83E−02 |
| L-Glutamic acid | 1.37E−01 |
| L-Glutamine | 2.94E+00 |
| Glycine | 2.94E−01 |
| L-Histidine-HCl—H2O | 1.18E−01 |
| L-Isoleucine | 3.26E−01 |
| L-Leucine | 3.54E−01 |
| L-Lysine hydrochloride | 3.91E−01 |
| L-Methionine | 9.06E−02 |
| L-Phenylalanine | 1.69E−01 |
| L-Proline | 2.16E−01 |
| L-Serine | 2.94E−01 |
| L-Threonine | 3.52E−01 |
| L-Tryptophan | 3.46E−02 |
| L-Tyrosine 2Na 2H2O | 1.68E−01 |
| L-Valine | 3.55E−01 |

TABLE 2-continued

Complete Formulation for TeSR1 Medium

| | mM |
|---|---|
| VITAMINS | |
| Ascorbic acid | 2.53E−01 |
| Biotin | 1.12E−05 |
| B12 | 3.94E−04 |
| Choline chloride | 5.03E−02 |
| D-Calcium pantothenate | 3.69E−03 |
| Folic acid | 4.71E−03 |
| i-Inositol | 5.49E−02 |
| Niacinamide | 1.30E−02 |
| Pyridoxine hydrochloride | 7.62E−03 |
| Riboflavin | 4.56E−04 |
| Thiamine hydrochloride | 2.42E−02 |
| GROWTH FACTORS/PROTEINS | |
| GABA | 9.79E−01 |
| Pipecolic Acid | 9.84E−04 |
| bFGF | 5.77E−06 |
| TGF beta 1 | 2.35E−08 |
| Human Insulin | 3.92E−03 |
| Human Holo-Transferrin | 1.37E−04 |
| Human Serum Albumin | 1.95E−01 |
| Glutathione (reduced) | 6.38E−03 |
| OTHER COMPONENTS | |
| Hypoxanthine Na | 1.18E−02 |
| Phenol red | 1.69E−02 |
| Putrescine-2HCl | 3.95E−04 |
| Thymidine | 1.18E−03 |
| 2-mercaptoethanol | 9.80E−02 |
| Pluronic F-68 | 2.33E−02 |
| Tween 80 | 3.29E−04 |

Certain components in the above formulation may also be substituted, e.g., in order to facilitate the use of TeSR for research or save money. For example, the medium mTeSR1 may be used with the present invention and differs from TeSR1 in the following ways: bovine serum albumin (BSA) is substituted for human serum albumin, and cloned zebrafish basic fibroblast growth factor (zbFGF) is substituted for bFGF. TeSR1 is described, e.g., in Ludwig et al. (2006), which is incorporated by reference herein in its entirety without disclaimer.

B. Matrix Component

Various matrix components may be used to culture and maintain human embryonic stem cells. For example, collagen IV, fibronectin, laminin, and vitronectin in combination may be used to provide a solid support for embryonic cell culturing and maintenance, as described in Ludwig et al. (2006), which is incorporated by reference in its entirety. Poly-L-lysine or CellStart™ (Invitrogen, Carlsbad, Calif.) may also be used as a matrix component.

Matrigel™ may also be used to provide a substrate for cell culture and maintenance of human embryonic stem cells. Matrigel™ is a gelatinous protein mixture secreted by mouse tumor cells and is commercially available from BD Biosciences (New Jersey, USA). This mixture resembles the complex extracellular environment found in many tissues and is used by cell biologists as a substrate for cell culture. Methods for human embryonic stem cell culture and maintenance are described, e.g., in Ludwig et al. (2006), which is incorporated by reference herein in its entirety. It is appreciated that additional methods for the culture and maintenance of human embryonic stem cells, as would be known to one of skill, may be used with the present invention.

II. HEMATOPOIETIC DIFFERENTIATION

Various methods may be used with the present invention for promoting differentiation of pluripotent cells into hematopoietic CD34+ stem cells. For example, pluripotent cells may be cultured on OP9 cells or mouse embryonic fibroblast cells. Alternately, hematopoietic progenitors may be cultured from pluripotent stem cells using a defined medium (e.g., containing one or more growth factors as described below and a matrix component such as fibronectin), or hematopoietic cells may be generated from pluripotent cells via the formation of embryoid bodies. In certain embodiments where it is desired to produce trypase-positive chymase-negative mast cells, murine fetal liver-derived stromal cells are preferably not used, as this may promote or result in differentiation into trypase-positive chymase-positive mast cells.

One method for the differentiation of hematopoietic progenitors from human ESCs involves culturing the ESCs on feeder cells, such as a mouse embryonic fibroblast (MEF) feeder layer or the mouse stromal cell line OP9, which induces robust differentiation to CD34+. Briefly, ESCs may be grown on MEFs in the presence of growth factors, and the MEFs provide a substrate and likely some nourishment for the cells. In contrast, use of OP9 cells do not require extra growth factors to induce CD34+ differentiation. The mechanisms by which these processes occur are not fully understood. This approach may also be used in combination with certain growth factors and serum (Wang, 2007). MEFs are also often used for culturing and maintaining human ESCs. Methods that utilize culture on mouse embryonic fibroblasts, such as the below protocol, may be modified to include Knockout™ serum replacement instead of FBS.

For example, the following protocol may be used for differentiation of pluripotent cells into hematopoietic cells. H1 cells may be routinely maintained on MEFs, and then passed onto almost confluent OP9 stromal cells in αMEM+20% defined FBS+100 ng/ml TPO at $1 \times 10^5$ cells/well (1 well is 9.6 cm$^2$). Cells may be fed with fresh medium at days 2 and 4. On day 7, cells may be split 1:3 onto fresh OP9 cells using collagenase IV. Cells may be fed with fresh medium at days 8 and 10. On day 11, cells may be split 1:1 onto fresh OP9 cells using collagenase IV, followed by Trypsin/EDTA to get single cells, and the medium may be changed to αMEM+10% defined FBS+100 ng/ml TPO. Cells may be fed by adding an additional 1 ml of this medium daily from days 14-16. In certain embodiments, methods for differentiation involving OP9 cells may be performed as described in Gaur et al., 2006, which is specifically incorporated by reference in its entirety.

Another approach for producing hematopoietic progenitors from human embryonic stem cells involves the formation of "embryoid bodies" (EB), or clusters of growing cells, in order to induce differentiation. In vitro aggregation of human ESC into EBs allows for the spontaneous and random differentiation of human ESC into multiple tissue types that represent endoderm, ectoderm, and mesoderm origins. Formation of three-dimensional EBs can thus be used to produce a fraction of hematopoietic cells. Pluripotent cells may be differentiated into embryoid bodies (EBs) by the following protocol: pluripotent cells may be grown to confluence and removed from the growth surface using dispase solution at about 2 mg/ml for about 20 minutes at about 37 degrees. Cells may be washed once to remove dispase, then resuspended in "EB formation medium" consisting of 85% IMDM, 15% FBS, 1% NEAA, and β-Mercaptoethanol. Cells in suspension may be added to Costar low attachment plates, where they can form embryoid bodies over the course of days, and fed every other day with ½ media change. At about day 12, EBs may be removed from culture and dissociated with collagenase IV, followed by trypsin/EDTA. Trypsin may then be neutralized with serum-containing media, and the cell suspension may be passed through a 22 G needle to further disrupt any remaining clumps. At this point, cells may be passed through a 100µ filter, and then a 30µ filter. CD34+ hematopoietic precursor cells obtained from the EBs may then be differentiated into mast cells via differentiation into megakaryocytes (e.g., using a MK#3 differentiation media) and then mast cells (e.g., using a mast cell differentiation media comprising SCF and IL6).

The following defined EB differentiation protocol may be used. Undifferentiated hESCs and iPSCs that adapted to feeder free growth on Matrigel coated plates may be harvested at confluence using TrypLE™ treatment for 6 minutes at 37° C. TRYPLE in the wells may be neutralized using EB basal media containing about 80% IMDM, about 20% BIT9500, about 1% NEAA, about 1 mM L-glutamine, and about 0.1 mM mercaptoethanol, about 0.75% BSA, about 50 µg/ml Ascorbic acid with about 0.25 mg/ml soybean trypsin inhibitor, and about 1 µM Rock inhibitor (H1152). The cells is suspension can be plated on to a Costar low attachment plates where they can form embryoid bodies between 12-24 hours. On the next day the cells EBs may be collected from each well by allowing the cells to settle down via gravity or via mild centrifugation. The supernatant may then be discarded and the EBs can then be placed EB-basal media supplemented with bone morphogenetic factor (BMP-4) and Vasular Endothelial Growth factor (VEGF), about 25 ng/ml for the first about 4-5 days of differentiation. The cells may be half-fed with fresh media every other day. The EBs cultures may be harvested on about day 5 and subjected to partial dissociation using TrypLE. The cells may then be washed free of TrypLE and switched to a second EB-differentiation media which is EB basal media supplemented with Flt-3 ligand (Flt-3L), interleukin-3 (IL-3), granulocyte macrophage, colony-stimulating factor (GM-CSF), for about the next seven days. The EB cultures may be half fed every other day for the next 7 days. The cells may be harvested after about 12-13 days of EB differentiation. The aggregates were digested to generate individualized cells using TrypLE. The single cell suspension may be stained for the presence of CD43, CD45, CD34, CD31 and the expression levels may be quantified by flow cytometry. Other methods for the generation of EBs include, e.g., the methods utilized in Lu et al. 2007 and Kennedy et al. 2007.

In other embodiments, hematopoietic progenitors may be cultured from pluripotent stem cells using a defined medium. Methods for the differentiation of pluripotent cells into hematopioetic CD34+ stem cells using a defined media are described, e.g., in U.S. Application 61/015,813, which is incorporated by reference in its entirety without disclaimer. It is anticipated that these methods may be used with the present invention.

For example, a defined medium may be used to induce hematopoietic CD34+ differentiation. The defined medium may contain the growth factors BMP-4, VEGF, bFGF, and a matrix component such as fibronectin. Defined culture media in which all or essentially all of the proteins present in the medium are all human may be used. The approaches used herein may be utilized in a single cell assay (from a colony based system), by including the ROCK inhibitors HA100 and H1152 to adhere single cells to a plate; for example, in these assay, hESC may be cultured in TeSR for three days without otherwise changing the other (colony-based system) parameters. These approaches may be automated using, e.g., robotic automation. As described in U.S. Application 61/015,813, the defined culture media may comprise BMP-4 in an amount of from about 5 ng/ml to about 200 ng/ml, or about 50 ng/ml, VEGF in an amount of from about 5 ng/ml to about 200 ng/ml, or about 50 ng/ml, and bFGF in an amount of from about 5 ng/ml to about 200 ng/ml, or about 50 ng/ml.

III. MEGAKARYOCYTE DIFFERENTIATION

The present invention provides methods for the differentiation of pluripotent cells into megakaryocytes, wherein a side population to the megakaryocytes may then be subsequently cultured under conditions to induce differentiation into mast cells. For example, the following paradigm may be used to induce differentiation of pluripotent cells into mast cells. Pluripotent cells may be subjected to a first differentiation protocol to initiate differentiation of the pluripotent cells, e.g., into hematopoietic progenitor cells. Next, the hematopoietic cells may be cultured cells under conditions to promote differentiation of the pluripotent cells into megakaryocytes and mast cells. Some of the same growth factors that are useful for promoting megakaryocyte differentiation are also important for mast cell differentiation. Finally, the initially small population of mast cells may be cultured and expanded under conditions to further promote differentiation into mast cells. In certain embodiments, the step of culturing the hematopoietic progenitors under conditions to promote differentiation into megakaryocytes may be excluded, and the hematopoietic progenitors may be cultured under conditions to promote differentiation into mast cells.

In the body, megakaryocytes are found in the blood marrow and produce platelets from processes, or proplatelets, which form on the cells. Megakaryocyte cells in the human body only represent a small fraction of bone marrow cells but can increase in number up to 10-fold in response to certain diseases. In the body, megakaryocytes typically differentiate from hematopoietic cells as follows: hemacytoclasts differentiate into megakaryoblasts, megakaryoblasts then differentiate into promegakaryocytes, and promegakaryocytes then differentiate into megakaryocytes.

Various media and methods may be used to differentiate pluripotent cells into megakaryocytes. For example, methods and media for differentiating pluripotent cells into megakaryocytes as described in US 2007/0077654, which is incorporated by reference in its entirety without disclaimer, may be used with the present invention.

Growth factors are preferentially included in a megakaryocyte differentiation medium. For example, a megakaryocyte differentiation medium may contain one, two, three, four, or all of FLT-3 ligand, stem cell factor (SCF), thrombopoietin (TPO), interleukin-3 (IL-3), and interleukin-6 (IL-6). In certain embodiments, only SCF may be included in a megakaryocyte differentiation medium. In other embodiments, SCF may be used in combination with one or both of IL-3 and/or IL-6. In various embodiments, FLT-3 ligand and/or TPO may be excluded from a megakaryocyte differentiation medium of the present invention.

It is anticipated that serum may be excluded from a megakaryocyte differentiation medium. Without wishing to be bound by any theory, it is anticipated that the exclusion of serum may result in an increased consistency in the results due to the elimination of variation in the contents between batches or lots of serum. Additionally, the exclusion of serum may result in the production of mast cells which, morphologically, appear to more consistently resemble mast cells in vivo. As stated above, in certain embodiments, Knockout™ serum replacement may be substituted for serum. The inventor specifically anticipates that using BIT9500 (Bovine serum albumin, Insulin, and Transferrin) to substitute for serum, pluripotent cells can be differentiated into mast cells (e.g., CD117/45+ and CD34 negative) according to the present invention.

Megakaryocyte differentiation may be performed as follows using CD34+ stem cells which have been differentiated from pluripotent cells. All cells in suspension, including the CD34+ cells, may be collected, centrifuged, and placed into MK#3 differentiation medium (containing 80% Stemline II, 20% BIT9500, L-glut, β-ME, Penstrep, FL3 100 ng/ml, SCF 100 ng/ml, TPO 100 ng/ml, IL3 10 ng/ml, and IL6 10 ng/ml) for approximately two weeks. Cells may be fed about every 4 days with at least a partial change to fresh medium. At the end of two weeks, cells may be assayed for expression of CD34, CD117, and CD45. As shown in the below examples, this approach can result in about 25% of mast cells, based on the expression by the cells of both CD45 and CD117, and the lack of expression of CD34.

IV. MAST CELL DIFFERENTIATION

Various approaches may be used according to the present invention for differentiating pluripotent cells into mast cells. In certain embodiments, pluripotent progenitor cells are first differentiated into hematopoietic cells, and the hematopoietic cells are subsequently differentiated into mast cells. The present invention also provides media ("mast cell differentiation media") for the differentiation of pluripotent-cell-derived hematopoietic progenitors or pluripotent-cell-derived megakaryocyte cells into mast cells.

A mast cell differentiation media preferably includes stem cell factor (SCF). In various embodiments, the mast cell differentiation media contains both SCF and IL-6. Other cytokines may be included in a differentiation media to promote mast cell differentiation including, for example IL-3, IL-4, IL-9 and/or IL-10.

As shown in the examples, a mast cell differentiation media containing SCF and IL-6 with no other growth factors was used to culture pluripotent-derived cells and resulted in a yield of approximately 90% or more of mast cells in the cell culture population. These mast cells were identified, e.g., by determining CD117(+), CD45(+), tryptase, and FcεRI (+) expression. The remaining proportion of the resulting cell population, as described in the below example 1, appear to be macrophages.

Culturing cells in a mast cell differentiation medium may be performed for various periods of time. For example, cells which have previously been cultured under conditions to promote megakaryocyte differentiation may be subsequently cultured in a mast cell differentiation medium for periods of about 5 days to 9 weeks, about 5 days to 4 weeks or more, about 5 days to about 3 weeks, about 1 week to about 3 weeks, about 1-2 weeks, or about 7, 8, 9, 10, 11, 12, 13, 14 days, or any range derivable therein. If pluripotent-cell-derived hematopoietic progenitors are cultured directly in a mast cell differentiation medium, then the cells may be cultured in a mast cell differentiation medium for about 1, 2, 3, 4, 5, 6, 7, 8, 9, 10 weeks or more, or any range derivable therein.

In certain embodiments the following protocol may be used to promote differentiation of pluripotent-derived cells into mast cells. Cells may be added to Mast Cell Differentiation Medium (90% RPMI, 10% defined FBS, 1% L-glut+BME, 1% Non Essential Amino Acids, 1% Penstrep, and 100 ng/ml each of SCF and IL6) and cultured for about 1-2 weeks or more.

In various embodiments, methods for differentiation of cord blood or peripheral blood into mast cells may also be used in combination with the present invention. For example, Schernthaner et al. (2001) describes methods for differentiating cord blood progenitors into mast cells using SCF in combination with IL-6 or (IL-4, IL-6, and IL-10) at various time points. Lappalainen et al. (2007) provides methods for differentiating peripheral blood into mast cells by culturing cells using SCF and other cytokines (IL-3, IL-6, IL-9, and IL-4) added for various periods of time. It is anticipated that either of these methods may be successfully used with the present invention.

V. DIFFERENTIATION MEDIA

Various media, including both defined and undefined media (i.e., including one or more animal product such as serum), may be used with the present invention to differentiate pluripotent cells into mast cells. Several steps may be involved in the process. For example, pluripotent cells may be maintained and then cultured under conditions to promote differentiation into hematopoietic progenitors; then the hematopoietic progenitors may be cultured under conditions to promote differentiation into mast cells. Alternately, pluripotent cells may be maintained and then cultured under conditions to promote differentiation into hematopoietic progenitors, which are then cultured under conditions to promote differentiation into megakaryocytes, and finally the megakaryocytes can be cultured under conditions to promote differentiation into mast cells.

In certain embodiments, serum may be excluded from the media (i.e., "serum free" media) and protocols of the present invention. Without wishing to be bound by any theory, it is anticipated that the exclusion of serum may result in an increased consistency in the results due to the elimination of variation in the contents between batches or lots of serum. Additionally, the exclusion of serum may result in the production of mast cells which, morphologically, appear to more consistently resemble mast cells in vivo.

In various embodiments, serum may be replaced with Knockout™ serum replacement or StemPro™ hESC SFM. Knockout™ serum replacement (SR) and StemPro™ hESC SFM are a defined serum-free formulation optimized to grow and maintain undifferentiated ES cells in culture and are available from Invitrogen (Carlsbad, Calif.). Knockout™ SR or StemPro™ hESC SFM may replace FBS. For example, Knockout™ SR may be used to support the growth of undifferentiated D3 ES cell colonies on inactivated mouse embryonic fibroblasts (see, e.g., Ezashi et al., 2005). In other embodiments, serum may be excluded from a media composition of the present invention. For example, in certain embodiments FBS may be excluded from culture conditions for inducing mast cell differentiation.

A. Growth Factors

Various growth factors are known in the art and may be used with the present invention. In certain embodiments, a differentiation medium such as a mast cell differentiation medium of the present invention may contain one, two, or all of the growth factors FLT-3 ligand, stem cell factor (SCF), thrombopoietin (TPO), interleukin-3 (IL-3), and interleukin-6 (IL-6).

Combinations of growth factors may be used to promote differentiation of progenitor cells into hematopoietic and/or megakaryocyte lineages prior to differentiation into mast cells. For example, using a mouse embryonic fibroblast culture system including media comprising TPO, with or without serum, may be used to initiate differentiation of pluripotent cells into hematopoietic progenitor cells. As described below, various combinations of growth factors may be included in a media to induce differentiation into megakaryocyte and/or mast cells.

In certain embodiments, the growth factors are recombinant growth factors which are exogenously added to a differentiation media. The growth factor(s) included in a differentiation media may be recombinant human growth factors. Alternately, the growth factor(s) may be non-human growth factors (e.g., mammalian, etc.) or a combination of human and non-human growth factors. In certain embodiments, non-human growth factors may be advantageously used, e.g., in instances where there is a cost-savings associated with the use of the non-human growth factor as compared to the analogous human growth factor.

1. Stem Cell Factor

Stem cell factor (SCF) is a cytokine which binds CD117 (c-Kit). SCF is also known as "KIT ligand," "c-kit ligand," or "steel factor." SCF exists in two forms: cell surface bound SCF and soluble (or free) SCF. Soluble SCF is typically produced in vivo by the cleavage of surface bound SCF by metalloproteases. SCF can be important for the survival, proliferation, and differentiation of hematopoietic progenitors and other hematopoietic progenitor cells. In vivo, SCF can change the BFU-E (burst-forming unit-erythroid) cells, which are the earliest erythrocyte precursors in the erythrocytic series, into the CFU-E (colony-forming unit-erythroid).

In certain embodiments, SCF is included in a culture medium of the present invention at a concentration of from about 5 to about 500 ng/ml, 25 to about 500 ng/ml, from about 25 to about 200 ng/ml, from about 50 to about 150 ng/ml, from about 25 to about 200 ng/ml, from about 75 to about 300 ng/ml, or any range derivable therein. In certain embodiments, SCF is included in the defined culture media at a concentration of about 25, 30, 35, 40, 45, 50, 55, 60, 65, 70, 75, 80, 85, 90, 95 or about 100 ng/ml.

2. IL-6

Interleukin-6 (IL-6) is a pro-inflammatory cytokine. In vivo, IL-6 is secreted by T-cells and macrophages and stimulates immune responses to trauma or other tissue damage leading to inflammation. IL-6 can also play a role in responses to certain bacterium, and osteoblasts secrete IL-6 in vivo to stimulate osteoclast formation. In humans, smooth muscle cells in the tunica media of many blood vessels can produce IL-6 as a pro-inflammatory cytokine, and IL-6 is an important in vivo mediator of fever.

In certain embodiments, IL-6 is included in a culture medium of the present invention at a concentration of from about 5 to about 500 ng/ml, 25 to about 500 ng/ml, from about 25 to about 200 ng/ml, from about 50 to about 150 ng/ml, from about 25 to about 200 ng/ml, from about 75 to about 300 ng/ml, or any range derivable therein. In certain embodiments, IL-6 is included in the defined culture media at a concentration of about 5, 10, 15, 20, 25, 30, 35, 40, 45, 50, 55, 60, 65, 70, 75, 80, 85, 90, 95 or about 100 ng/ml.

3. IL-3

Interleukin-3 (IL-3) is a hemopoietic growth factor involved in the survival, proliferation and differentiation of multipotent hemopoietic cells. In five mammalian species, including man, the gene encoding IL-3 has been isolated and expressed to yield the mature recombinant proteins. The human IL-3 gene encodes a protein of 133 amino acids with two conserved cysteine residues and 2 potential N-linked glycosylation sites (Wagemaker et al., 1990).

In certain embodiments, IL-3 is included in a culture medium of the present invention at a concentration of from about 5 to about 500 ng/ml, 25 to about 500 ng/ml, from about 25 to about 200 ng/ml, from about 50 to about 150 ng/ml, from about 25 to about 200 ng/ml, from about 75 to about 300 ng/ml, or any range derivable therein. In certain embodiments, IL-3 is included in the defined culture media at a concentration of about 5, 10, 15, 20, 25, 30, 35, 40, 45, 50, 55, 60, 65, 70, 75, 80, 85, 90, 95 or about 100 ng/ml.

4. FLT-3 Ligand

FLT-3 ligand, also referred to as FLT3 ligand, is the endogenous ligand for FLT3. FLT3 is a receptor tyrosine kinase expressed by immature hematopoietic progenitor cells. The ligand for FLT3 is a transmembrane or soluble protein and is expressed by a variety of cells including hematopoietic and marrow stromal cells; in combination with other growth factors, FLT-3 ligand can stimulate the proliferation and development of stem cells, myeloid and lymphoid progenitor cells, dendritic cells and natural killer cells. Activation of the receptor leads to tyrosine phosphorylation of various key adaptor proteins known to be involved in different signal transduction pathways that control proliferation, survival and other processes in hematopoietic cells. FLT3 and mutations affecting FLT3 are also important in pathological diseases, such as the prognosis and therapy of leukemia (Drexler et al., 2004).

In certain embodiments, FLT-3 ligand is included in a culture medium of the present invention at a concentration of from about 5 to about 500 ng/ml, 25 to about 500 ng/ml, from about 25 to about 200 ng/ml, from about 50 to about 150 ng/ml, from about 25 to about 200 ng/ml, from about 75 to about 300 ng/ml, or any range derivable therein. In certain embodiments, FLT-3 ligand is included in the defined culture media at a concentration of about 25, 30, 35, 40, 45, 50, 55, 60, 65, 70, 75, 80, 85, 90, 95 or about 100 ng/ml. In certain embodiments, inclusion of FLT-3 ligand is included in the media for the first ~1-3 weeks in the culture of pluripotent cells, after which time it can be removed from the system with no detrimental effect on differentiation.

5. Thrombopoietin

Thrombopoietin (TPO) is a glycoprotein hormone which is produced in vivo primarily by the liver and the kidneys and regulates the production of platelets by the bone marrow. TPO can stimulate in vivo the production and differentiation of megakaryocytes, the bone marrow cells that fragment into large numbers of platelets. In certain embodiments, inclusion of TPO is included in the media for the first approximately ~1-3 weeks in the culture of pluripotent cells, after which time it can be removed from the system with no detrimental effect on differentiation.

In certain embodiments, TPO is included in a culture medium of the present invention at a concentration of from about 5 to about 500 ng/ml, 25 to about 500 ng/ml, from about 25 to about 200 ng/ml, from about 50 to about 150 ng/ml, from about 25 to about 200 ng/ml, from about 75 to about 300 ng/ml, or any range derivable therein. In certain embodiments, TPO is included in the defined culture media at a concentration of about 25, 30, 35, 40, 45, 50, 55, 60, 65, 70, 75, 80, 85, 90, 95 or about 100 ng/ml.

6. Other Growth Factors

In addition to the growth factors listed above, one or more of IL-3, IL-4, IL-9, IL-10, and/or erythropoietin (EPO) may be included in a differentiation media such as a mast cell differentiation media. The other growth factor(s) may be included in a culture medium of the present invention at a concentration of from about 5 to about 500 ng/ml, 25 to about 500 ng/ml, from about 25 to about 200 ng/ml, from about 50 to about 150 ng/ml, from about 25 to about 200 ng/ml, from about 75 to about 300 ng/ml, or any range derivable therein. In certain embodiments, TPO is included in the defined culture media at a concentration of about 25, 30, 35, 40, 45, 50, 55, 60, 65, 70, 75, 80, 85, 90, 95 or about 100 ng/ml.

B. Other Components

A differentiation culture medium of the present invention may also contain additional components such as nutrients, amino acids, antibiotics, buffering agents, and the like. In various embodiments, a differentiation culture medium may contain one or more vitamin, mineral, salt, lipid, amino acid, or other component. In certain embodiments a culture medium of the present invention may contain non-essential amino acids, L-glutamine, Pen-strep, and monothioglycerol.

Serum, such as fetal bovine serum (FBS), may be included in a media according to the present invention at, e.g., a concentration of about from about 10% to about 30%. In certain embodiments, about 20% serum is included in a media, e.g., for the maintenance of pluripotent cells.

Stemline II™ may be included in a media of the present invention, e.g., at a concentration of from about 70% to about 90%. Stemline™ II Hematopoietic Stem Cell Expansion Medium is available from Sigma-Aldrich (St. Louis, Mo.). This formulation can be used to increase in the number of cells expanded from cord blood CD34+ cells, as well as 4-HC purged CD34+ cells from peripheral blood (PBPC) products. StemlineII™ Hematopoietic Stem Cell Expansion Medium is a proprietary formulation without antibiotics and cytokines.

BIT 9500 (StemCell Technologies Inc., Vancouver, Canada) may also be included in a culture medium of the present invention, e.g., in an amount of about from about 10% to about 30%, or in an amount of about 20%. BIT 9500 contains pre-tested batches of bovine serum albumin, insulin and transferrin (BIT) in Iscove's MDM. BIT 9500 contains 50 mg/mL bovine serum albumin (buffered with NaHCO3), 50 μg/mLrh insulin, 1 mg/mL human transferrin (iron-saturated). In certain embodiments, KOSR may be substituted for BIT 9500 in embodiments where a defined medium is not required. KOSR is an undefined medium which is commercially available (e.g., from Gibco/Invitrogen, catalog #10828) and has been described previously in WO98/30679.

The use of BIT, as described above, may be replaced by HIT; HIT includes the compositions described about in BIT, with the exception that the components, such as serum albumin, are human components (e.g., human serum albumin). However, since many of the applications for mast cells differentiated according to the present invention are related to research purposes, BIT may be a less expensive alternative to HIT when human components are not required.

C. Defined Methods for Mast Cell Production

Mast cells may be differentiated from hESC or iPS cells using defined conditions which do not utilize animal products such as serum. In particular, the inventor has discovered that certain growth factors are particularly important for the differentiation of pluripotent cells which have been maintained under defined conditions. In certain embodiments, pluripotent cells may be sequentially exposed to several defined media to promote differentiation into hematopoietic precursor cells. After culture and maintenance of the pluripotent cells in an essentially undifferentiated state in a first defined media (e.g., in a TeSR media), the cells may be exposed to a second defined media containing no or essentially no BMP4, VEGF, IL3, Flt3 ligand, or GMCSF. The cells may then be exposed to a third defined media comprising BMP4, VEGF, IL3, Flt3 ligand, and GMCSF to promote hematopoietic differentiation; alternately, the cells may be exposed to a third defined media comprising BMP4 and VEGF, followed by exposure to a fourth media comprising IL3, Flt3 ligand, and GMCSF. The inventor has discovered that sequential exposure to a third defined media comprising BMP4 and VEGF, followed by exposure to a fourth media comprising IL3, Flt3 ligand, and GMCSF can surprisingly result in substantial increases in the generation of hematopoietic precursor cells. The inventor has also discovered that hypoxic conditions (e.g., exposure to an atmospheric pressure of less than about 20%, or about 5% $O_2$), reaggregation of cells (e.g., using trypsin or TrypLE™), and formation of aggregates using defined ranges of cells in the formation of embryoid bodies (e.g., from about 200-1000 cells per aggregate) can further promote differentiation into hematopoietic precursor cells.

In certain embodiments, the following methods may be used to differentiate hESC or iPS cells into mast cells under defined conditions. First, undifferentiated hESCs and iPSCs that adapted to feeder free growth on Matrigel™ coated plates may be harvested at confluence using trypsin or TRYPLE treatment (e.g., TrypLE™ Express for about 5-15 minutes or about 6 minutes at 37° C.). The treatment with trypsin or TrypLE may act to substantially individualize the cells or dissociate the cells into single cells or clumps containing about 2-10 cells. TrypLE may then be neutralized using EB basal media containing IMDM supplemented with 20% BIT9500 (Stem Cell Technologies), 1% NEAA, 1 mM L-glutamine, and 0.1 mM mercaptoethanol, 0.75% BSA, 50 ug/ml ascorbic acid. To facilitate EB formation the cells may be re-suspended in EB basal media supplemented with a Rho-associated kinase (ROCK) inhibitor (e.g., about 1 μM H1152) and a trypsin inhibitor (e.g., about 0.25 mg/ml soybean trypsin inhibitor) following trypsin or TRYPLE treatment. Cell viability may be determined and the resulting cell suspension may be plated in low attachment plates for about 1-3 days (e.g., about 24 hours).

ROCK inhibitors which may be used above include HA-100 (1-(5-isoquinolinesulfonyl)piperazine hydrochloride), Y-27632 (N-(4-Pyridyl)-N'-(2,4,6-trichlorophenyl) urea, 3-(4-Pyridyl)-1H-indole), and H-1152 ((S)-(+)-2-Methyl-1-[(4-methyl-5-isoquinolinyl)sulfonyl] homopiperazine), H-7, iso H-7, H-8, H-9, H-89, HA-1004, and HA-1077. The ROCK inhibitor may be present in an ES cell growth media, e.g., at a concentration of about 1-15 μM, 5-15 μM, 1-30 μM, 5-30 μM, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 μM, or any range derivable therein. In certain embodiments, HA-100 or Y-27632 is present in an ES cell growth media at about 10-20 μM.

The cells EBs may then be collected from each well and the cell suspension may be centrifuged. The cells may be resuspended in EB-differentiation media which is EB basal media supplemented with 25 ng/ml bone morphogenetic factor (BMP-4) 25 ng/ml and vasular endothelial growth factor (VEGF), 25 ng/ml for the first about 3-5 days (e.g., about 4 days) of EB differentiation. The cells may be half fed with fresh media every other day. Varying amounts of BMP-4 and VEGF may be included in the media (e.g., about 10-50 ng/ml BMP4; about 10-50 ng/ml VEGF).

The EB cultures may be harvested on day 5 and subjected to partial dissociation using TrypLE™ or trypsin. The cells may then be washed free of TrypLE™ or trypsin and switched to a second EB-differentiation media which is EB basal media supplemented with 25 ng/ml Flt-3 ligand (Flt-3L), 10 ng/ml interleukin-3 (IL-3), 10 ng/ml granulocyte macrophage, and colony-stimulating factor (GM-CSF) for the next about 5-10 days (e.g., about seven days). The EB cultures may be half-fed other day and the cells for the next about 5-10 days (e.g., about seven days). The cells may be harvested after about 12-13 days of EB differentiation; the aggregates may then be digested to generate individualized cells using TrypLE™ or trypsin. The single cell suspensions may be stained for the presence of CD43, CD45, CD34 and/or CD31, and expression levels may be quantified using flow cytometry. Varying amounts of IL3, Flt3 ligand, and GMCSF may be included in the media (e.g., 5-25 ng/ml IL3, about 10-50 ng/ml Flt3 ligand, and about 5-25 ng/ml GMCSF).

The individualized cells may then be plated to a new low attachment plate containing MK3 media (e.g., for about 10-21 days, or about two weeks). The MK3 media contains IMDM media supplemented with about 20% BIT9500, about 1% L-Glutamine, about 0.1 mM β mercaptoethanol, about 100 ng/ml of each of Flt-3 ligand (Flt-3L), stem cell factor (SCF), and thrombopoietin (TPO) along with about 10 ng/ml of each of interleukin-3 (IL-3) and interleukin-6 (IL-6). The cells may be half-fed with fresh media every four days. The cells may then be harvested at the end of about 10-21 days (e.g., about two weeks) and the expression of CD34, Cd117 and CD45 may be quantified by flow cytometry.

Mast cells may then be enriched by the following method. Following the two week expansion in MK3 media the cells may be harvested and placed in mast cell media containing StemPro™ media supplemented with 100 ng/ml Stem cell factor (SCF) and interleukin-3 (IL-6). The cells may be expanded in the mast cell media (e.g., for an additional 1-5 weeks, or from about 2-3 weeks). During this process the cells may be half-fed with fresh media (e.g., every four days). The percentage of CD34, Cd117 and CD45 positive may be quantified by flow cytometry. As shown in the below examples, these methods may be used to generate CD117(+) CD45(+) CD34(−) mast cells which stain for trypase.

VI. SEPARATION OF MAST CELLS

After preparation of mast cells from pluripotent cells, it may be desirable to purify the mast cells. Methods for separation of cells using flow cytometry, such as FACS, or magnetic activated cell sorting may be used to separate hematopoietic cells from a heterogeneous cell population.

A. Magnetic Activated Cell Sorting (MACS)

Mast cells may be isolated from differentiated hESCs using a magnetic activated cell sorter (MACS). MACS typically utilizes an antibody, such as an anti-CD117 antibody, in combination with magnetic beads to separate cells over a column. MACS may, in certain embodiments, be more gentle on cells and favorably affect cell viability and integrity as compared to FACS, possibly due to the laser illumination of cells involved with FACS.

Various MACS products are commercially available, including MACS MicroBeads™ columns or AutoMACS™ (Miltenyi Biotec, CA, USA), which may be used according to the manufacturer's instructions. PBS/0.5% BSA (with or without EDTA) may used as the buffer for cell isolation. In some experiments, a Dead Cell Removal Kit (Miltenyi Biotec) may be used to remove dead cells prior to isolation of CD117+/CD45+ cells. Repeated MACS columns may be used if necessary.

B. FACS

Fluorescence activated cell sorting (FACS) may also be used to separate mast cells. FACS utilizes the degree or fluorescence exhibited by a cell, e.g., due to bound anti-CD117 or an anti-CD45 antibody comprising a fluorescent tag, to separate cells. In this way FACS may be used to separate CD117+/CD45+ mast cells from a heterogeneous cell population.

The following protocol may be used to perform FACS to quantify hematopoietic cells. Cells may be prepared in PBS containing 1% FBS or 0.5% BSA, and labeled for 15-30 minutes at 4° C. with a combination of monoclonal antibodies (mAbs). A 1:50 dilution for specific antibodies, and 1:200 dilution for IgG control may be used. The samples may be analyzed by a FACSCalisbur (Becton Dickson).

VII. IDENTIFICATION OF MAST CELLS

A variety of methods may be used for the identification of mast cells, including identification of cell surface markers and/or evaluation of the biological function of mast cells. For example, mast cells are characterized by the expression of certain cell-surface markers. The term "mast cells," as used herein, refers to cells which test positive for CD117 (also referred to as "c-kit"), FcεRI, tryptase, and CD45 expression, while being negative for CD34 expression. As would be appreciated by one of skill, these cell surface markers can be evaluated using methods including immunological tests (e.g., western blot, ELISA, etc.). In various embodiments, the present invention provides methods for differentiating pluripotent cells into mast cells which are CD45+, CD117+, tryptase+, and CD34(−). The FcεRI may or may not be expressed on the mast cells, depending on the maturity of the mast cells. More specifically, FcεRI are typically expressed in more mature mast cells. In certain embodiments, mast cells may be differentiated into embryonic mast cells, juvenile mast cells, mature mast cells, and/or mast like cells (i.e., cells which are CD45+, CD117+, tryptase+, and CD34(−), but lack one or more typical characteristic of mast cells). Pluripotent cells may be differentiated via the methods disclosed herein into tryptase-positive chymase-negative mast cells or tryptase-positive chymase-positive mast cells.

Mature mast cells may be identified by cell surface expression of the high-affinity receptor FcεRI. FcεRI identifies and binds the Fc region of immunoglobulin-E (IgE). The very high affinity of FcεRI for IgE molecules typically results in mast cells being coated with IgE. IgE are produced by B-cells (the antibody-producing cells of the immune system).

Mast cells can further be characterized by evaluation of biological function. For example, mast cells may be identified or characterized by evaluating histamine release, metachromatic staining (e.g., using toluidine blue) for granules, detecting chymase and/or cathepsin G. Expression of heparin, histamine, tryptase, chymase, and cathespin G in secretory granules may be evaluated and indicate mast cell identity. Mast cells are also characterized by their ability to acutely release histamine in response to stimulation with IgE-anti-IgE, compound 48/80, substance P, and/or the anaphylatoxin C3a.

VIII. BIOREACTORS AND ROBOTIC AUTOMATION

One or more steps for the production of mast cells from progenitor cells such as hESC or iPSC may be automated. Automating a process using robotic or other automation can allow for more efficient and economical methods for the production, culture, and differentiation of cells. For example, robotic automation may be utilized in conjunction with one or more of the culture of human embryonic stem cells, passaging, addition of media, addition of differentiation media, culture in differentiation media, and separation of cell type, e.g., using magnetic separation or FACS.

A bioreactor may also be used in conjunction with the present invention to culture, maintain, and/or differentiate cells (e.g., human embryonic stem cells, CD34+ cells, hematopoietic cells, etc.) according to the present invention. Bioreactors provide the advantage of allowing for the "scaling up" of a process in order to produce an increased amount of cells. Various bioreactors may be used with the present invention, including batch bioreactors, fed batch bioreactors, continuous bioreactors (e.g., a continuous stirred-tank reactor model), and/or a chemostat.

In certain embodiments, the Tecan Cellerity™ system may be used with the present invention. hESCs may be cultured on the robot, using flat plates in order to induce differentiation into hematopoietic precursor cells. Once separation of the cells has occurred, spinner flasks or a bioreactor may be used to generate large numbers of cells.

Robotic automation specifically envisioned for use with the present invention may be obtained from, for example, Tecan (CA, USA). Robotics may include liquid handling tools such as cap-piercing probes and disposable tips to minimize carry-over between samples. In various embodiments, robotics may be utilized in conjunction with one or more bioreactor for culturing cells (e.g., during the maintenance or growth of hESCs, the differentiation of hESCs into hematopoietic precursor cells, and/or the differentiation of hematopoietic cells into single-positive or double-positive mast cells, etc.).

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Mast Cells Derived from Human Embryonic Stem Cells

Mast cells derived from human embryonic stem cells are a cell type not previously characterized from human embryonic stem cells. Our mast cells have the potential to be amplified to relatively large numbers and the ability to be purified. In contrast to this, mast cells from the human body are not found in great numbers, and they reside in tissues which makes isolation difficult.

Generation of mast cells was performed using the following three step differentiation protocol:

H1 cells were routinely maintained on MEFs, and then passed onto almost confluent OP9 stromal cells in αMEM+ 20% defined FBS+100 ng/ml TPO at $1 \times 10^5$ cells/well (1 well is 9.6 cm$^2$). Cells were fed with fresh medium at days 2 and 4. On day 7, cells were split 1:3 onto fresh OP9 cells using collagenase IV. Cells were fed with fresh medium at days 8 and 10. On day 11, cells were split 1:1 onto fresh OP9 cells using collagenase IV, followed by Trypsin/EDTA to get single cells, and the medium was changed to αMEM+10% defined FBS+100 ng/ml TPO. Cells were fed by adding an additional 1 ml of this medium daily from days 14-16.

At day 16, all cells in suspension were collected and centrifuged, and placed into MK#3 differentiation medium (80% Stemline II, 20% BIT9500, L-glut, 13-ME, Penstrep, FLT-3 100 ng/ml, SCF 100 ng/ml, TPO 100 ng/ml, IL3 10 ng/ml, and IL6 10 ng/ml) for approximately two weeks. Cells were fed about every 4 days with at least a partial change to fresh medium. At the end of two weeks, cells were assayed for expression of CD34, CD117, and CD45. About 25% of cells expressed both CD45 and CD117, and lacked CD34, which is a profile consistent with mast cells.

Cells were then added to Mast Cell Differentiation Medium (90% RPMI, 10% defined FBS, 1% L-glut+BME, 1% Non Essential Amino Acids, 1% Penstrep, and 100 ng/ml each of SCF and IL6). Cells were assayed for the above markers weekly, and after another 12 days, the cells were 93% positive for CD117 and CD45, while being negative for CD34. At this time a Wright stain was done to check the morphology of the cells, and morphology was consistent with mast cells (basophilic staining/dark purple granules). Tryptase is present in mast cell granules, and is unique to mast cells, so a stain to detect tryptase was also done at this time. Bright staining was observed, and the percentage of cells staining positive was consistent with the CD117/CD45+ population (about 90%). Cells were tested a few weeks later for expression of FcεR1, and expression was able to be stimulated by addition of IL4 to the culture, and further stimulated by addition of IgE to the culture. Results indicate that the remaining 10% of cells in the population are macrophages. Mast cells were capable of releasing granules (as measured by beta-hexosaminidase) in response to immunologic (IgE-NP/BSA-NP) stimulation, as well as in response to chemicals compound 48/80 and substance P. The inventors envision that the cells will respond in a dose-dependent manner, and studies are underway to evaluate the dose-response relationship.

Additional characterization of the resulting cells may be performed by evaluating features of the cells including: histamine release, metachromatic staining (toluidine blue) for granules, presence of chymase and cathepsin G, and expression of the high affinity receptor FcεR1.

Example 2

Characterization of hESC-Derived Mast Cells and CD34+Derived Mast Cells

Properties of hESC-derived mast cells, produced by the method described in Example 1, were compared with CD34+ derived mast cells, produced by the method disclosed in Jensen et al., 2008. The results of these tests indicate that, while some variation in characteristics were observed between the hESC-derived and CD34+ derived mast cells (e.g., variation in staining or expression levels for certain markers), both the hESC-derived mast cells and the CD34+ derived mast cells were shown to be functional mast cells.

Both hESC-derived and CD34+ derived mast cells stained for toluidine blue, which is a marker of granules. Additionally, both hESC-derived and CD34+ derived mast cells were observed to be c-kit positive, and both hESC-derived and CD34+ derived mast cells were observed to express FcεR1. The hES cell derived mast cells were observed, on average, to express FcεR1 at lower levels than CD34+ derived mast cells, but some variation in FcεR1 expression was observed between batches.

Degranulation was also evaluated. Cells were starved overnight using cytokine-free STEMPRO media. Cells were next incubated overnight with Biotinylated human IgE (100 ng/ml). Cells were then triggered for degranulation for 30 minutes with streptavidin in absence and presence of SCF. Degranulation was then measured by release of α-hexosaminidase. As shown in FIGS. 1A-C, both hESC-derived and CD34+ derived mast cells degranulate in a dose-dependent manner, although hES cell derived mast cells appeared to degranulate at an overall lower level.

Cytokine production was evaluated. Cells were incubated overnight with Biotinylated human IgE (100 ng/ml). Cells were then triggered for cytokine production for 6 h with streptavidin in presence of SCF. Cytokine release was measured by ELISA. As shown in FIGS. 2A-B, both hESC-derived and CD34+ derived mast cells displayed production of IL-8 and GMCSF production, although somewhat increased CM-CSF and reduced IL-8 production was observed in the hESC-derived mast cells, as compared to the CD34+ derived mast cells.

Calcium flux was further evaluated. Cells were starved overnight in cytokine-free STEMPRO media, and cells were incubated overnight with Biotinylated human IgE (100 ng/ml). Cells were loaded with Fura 2, and cells were activated and fluorescence was measured. As shown in FIGS. 3A-B, the hESC-derived mast cells displayed reduced calcium flux as compared to CD-34+ derived mast cells.

LAT phosphorylation was also measured in the mast cells. Cells were starved overnight in cytokine-free STEMPRO media. Cells were incubated overnight with Biotinylated human IgE (100 ng/ml), and cells were triggered for 2 minutes with streptavidin (100 ng/ml) and/or SCF (30 ng/ml). Protein phosphorylation was tested in several targets, including: p-Kit, p-AKT, p-Btk, pERK1/2, pp 38, pLAT, pNTAI (LAT2), and total Syk were measured, and results are shown in FIG. 4. LAT phosphorylation was not observed in the mast cells. It is possible that this result may be due to using H1 cells. Although initial chymase staining experiments were inconclusive, additional experiments are underway.

Example 3

Defined Methods for Production of hESC-Derived Mast Cells hESC-derived mast cells were produced using the following protocol for EB formation and subsequent differentiation:

Step 1: Undifferentiated hESCs and iPSCs that were adapted to feeder free growth on Matrigel coated plates were harvested at confluence using TrypLE treatment for 6 minutes at 37° C. Tryple E in the wells was neutralized using EB basal media containing IMDM supplemented with 20% BIT9500 (Stem Cell Technologies), 1% NEAA, 1 mM L-glutamine, and 0.1 mM mercaptoethanol (all from Invitrogen, Carlsbad, Calif.), 0.75% BSA, 50 ug/ml Ascorbic acid. To facilitate EB formation the cells were resuspended in EB basal media supplemented with 1 µM Rock inhibitor (H1152), Soybean trypsin inhibitor (0.25 mg/ml) following Trypsin treatment. The cell viability was determined and the resulting cell suspension was plated in low attachment plates for 24 hours.

Step 2: On the next day the cells EBs were collected from each well and the cell suspension was centrifuged. The cells were resuspended in EB-differentiation media which is EB basal media supplemented with 25 ng/ml bone morphogenetic factor (BMP-4) 25 ng/ml and Vasular Endothelial Growth factor (VEGF), 25 ng/ml for the first 4 days of EB differentiation. The cells were half fed with fresh media every other day.

Step 3: The EBs cultures were harvested on day 5 and subjected to partial dissociation using TrypLE. The cells were washed free of TrypLE and switched to a second EB-differentiation media which is EB basal media supplemented with 25 ng/ml Flt-3 ligand (Flt-3L), 10 ng/ml interleukin-3 (IL-3), 10 ng/ml granulocyte macrophage, colony-stimulating factor (GM-CSF), for the next seven days. The EB cultures were half fed other day and the cells for the next 7 days. The cells were harvested after 12-13 days of EB differentiation; the aggregates were digested to generate individualized cells using TrypLE. The single cell suspension was stained for the presence of CD43, CD45, CD34, CD31 and the expression levels was quantified by flowcytometry.

Step 4: The individualized cells were plated to a new low attachment plate containing MK3 media for the next two weeks. The MK#3 media contains IMDM media supplemented with BIT9500 20%, L-Glutamine 1%, 0.1 mM β mercaptoethanol 100 ng/ml Flt-3 ligand (Flt-3L), Stem cell factor (SCF); and Thrombopoietin (TPO) along with 10 ng/ml of 10 ng/ml interleukin-3 (IL-3) and interleukin-3 (IL-6). The cells were half fed with fresh media every four days. The cells were harvested at the end of two weeks and the presence of CD34, Cd117 and CD45 positive were quantified by flow cytometry.

Step 5: Mast cell enrichment: Following the two week expansion in MK3 media the cells were harvested and placed in mast cell media containing Stem Pro media supplemented with 100 ng/ml Stem cell factor (SCF) and interleukin-3 (IL-6). The cells were expanded in the mast cell media for additional two to three weeks. During the entire process the cells were half fed with fresh media every four days. The percentage of CD34, Cd117 and CD45 positive were quantified by flow cytometry.

Cytospins: Cells were fixed and stained with to detect the presence of Tryptase positive cells. As a result of the flow cytometry analysis of H1 cells in mast cell media, the H1 cells stained for the presence of CD117(+)/CD45(+) and CD34(−) cells in mast cell media. Tryptase staining of H1 cells in mast cell media was also observed.

Example 4

Embryoid Body (EB) Derived Mast Cells

H1 p43 cells were grown to confluence and removed from the growth surface using dispase solution at 2 mg/ml for 20 minutes at 37 degrees. Cells were washed once to remove dispase, then resuspended in "EB formation medium" consisting of 85% IMDM, 15% FBS, 1% NEAA, and β-Mercaptoethanol. Cells in suspension were added to Costar low attachment plates, where they formed embryoid bodies over the course of days, and fed every other day with ½ media change. At day 12, EBs were removed from culture and dissociated with collagenase IV, followed by trypsin/EDTA. The Trypsin was neutralized with serum-containing media, and the cell suspension was passed through a 22 G needle to further disrupt any remaining clumps. At this point, cells were passed through a 100µ filter, and then a 30µ filter.

Cells were resuspended in MACS Buffer in preparation for cell separation using the CD34 ligand. Cells were stained with magnetic beads and passed through a succession of two magnetic columns to purify CD34+ cells. Approximately 10% of cells expressed CD34. The cells not expressing CD34 were discarded, and the cells expressing CD34 were placed into megakaryocyte differentiation medium (MK#3), which consists of 80% Stemline II (Sigma), 20% BIT9500 (Stem-Cell Technologies), 1% Penstrep, 1% L-glutamine with β-ME, 100 ng/ml each of SCF, TPO, and FL3, and 10 ng/ml each of IL3 and IL6. Heparin is also included. Cells were allowed to grow in this medium for 12 days.

At day 12, cells were removed from MK#3, and transferred both to Mast Cell Medium (90% RPMI, 10% FBS, 100 ng/ml each of SCF and IL6, and 1% each of NEAA, Penstrep, and L-glut+β-ME), and StemPro Mast Cell Medium (StemPro medium with supplement (Gibco), 100 ng/ml each of SCF and IL6, and 1% each of Penstrep and L-glut+β-ME). The StemPro was used to see if our mast cells could be differentiated and expanded using serum-free conditions. Cells were grown in these media for more than two weeks (are still in culture) and were periodically tested for expression of CD34, CD117, and CD45, and were also tested for expression of Tryptase.

Cells were positive for tryptase, negative for CD34, and positive for both CD45 and CD117. These results were obtained via tryptase staining and flow cytometry.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Publn. 2006/0084168
U.S. Publn. 2007/0077654
U.S. Publn 2009/0081784
Conti et al., *Ann. Clin. Lab. Sci.*, 37(4):315-322, 2007.
Dahl et al., *J. Immunol. Methods*, 262:137-143, 2002.
Drexler et al., *Growth Factors*, 22(2):71-73, 2004.
Ezashi et al. *Proc. Natl. Acad. Sci. USA*, 102(13): 4783-4788, 2005.
Huangfu et al. *Nat. Biotechnol.* 26(11):1269-75, 2008.
Kambe et al., *J. Immunol. Methods*, 240:101-110, 2000.
Jensen et al., *J Pharmacol Exp Ther.* 324(1):128-38, 2008.
Lappalainen et al., *Clin. Experim. Allergy*, 37:1404-1414, 2007.
Ludwig et al., *Nature Biotech.*, (2):185-187, 2006a.
Ludwig et al., *Nature Methods*, 3(8):637-646, 2006b.
Nakagawa et al. *Nat. Biotechnol.*, 26(1):101-106, 2008.
Schernthaner et al., *Blood*, 98:3784-3792, 2001.
Takahashi et al., *Cell*, 131(5):861-872, 2007.
Takahashi et al., *Nat. Protoc.*, 2(12):3081-3089, 2007.
Wagemaker et al., *Biotherapy*, 2(4):337-345, 1990.
Wang et al., *J. Immunol. Methods*, 309:69-74, 2006.
Wang et al., *Nature Biotech.*, 25(3):317-318, 2007.
Yu et al. *Science*, 318(5858):1917-1920, 2007.
Lu, et al. *Nature Methods*, 4(6):501-509, 2007.
Kennedy et al. *Blood.* 109(7): 2679-2687, 2007.
Zhou et al. *Cell Stem Cell*. Apr. 22, 2009. [epub]

What is claimed is:

1. A method of preparing human mast cells by culturing human pluripotent cells in vitro comprising the steps of:
   a) culturing human pluripotent cells under conditions that promote differentiation of the cells into hematopoietic progenitor cells or megakaryocytes, to provide a first cell population comprising hematopoietic precursors or megakaryocytes; and
   b) culturing the first cell population under conditions that promote the differentiation into mast cells, to provide a second cell population comprising mast cells;
   wherein the step (a) culturing step does not employ a co-culture with murine fetal liver-derived stromal cells as a feeder layer;
   wherein the step (b) culturing step comprises culturing the cells in a media comprising stem cell factor;
   further wherein the pluripotent cells are cultured in a media comprising TPO.

2. A method of preparing human mast cells by culturing human pluripotent cells in vitro comprising the steps of:
   a) culturing human pluripotent cells under conditions that promote differentiation of the cells into hematopoietic progenitor cells or megakaryocytes, to provide a first cell population comprising hematopoietic precursors or megakaryocytes; and
   b) culturing the first cell population under conditions that promote the differentiation into mast cells, to provide a second cell population comprising mast cells;
   wherein the step (a) culturing step does not employ a co-culture with murine fetal liver-derived stromal cells as a feeder layer;
   wherein the step (b) culturing step comprises culturing the cells in a media comprising stem cell factor;
   further wherein step (a) comprises culturing the pluripotent cells under defined conditions and the sequential steps of:
   1) culturing or maintaining a plurality of the pluripotent cells in a first defined media comprising at least one growth factor;
   2) culturing the cells incubated in step 1) in a second defined media comprising an amount of BMP4 and VEGF sufficient to expand or promote differentiation in a plurality of the cells; and
   3) culturing the cells cultured in step 2) in a third defined media comprising an amount of IL3, Flt3 ligand, and GMCSF sufficient to expand or promote differentiation in a plurality of the cells;
   wherein a plurality of the pluripotent cells are differentiated into hematopoietic precursor cells.

3. The method of claim 2, wherein the second cell population comprises tryptase-positive mast cells.

4. The method of claim 2, wherein at least some of the cells are at least partially separated or are substantially individualized prior to step (b).

5. The method of claim 4, wherein the cells are substantially individualized using an enzyme.

6. The method of claim 5, wherein the enzyme is a trypsin or TRYPLE.

7. The method of claim 5, wherein the cells are contacted with a ROCK inhibitor and a trypsin inhibitor subsequent to said individualization.

8. The method of claim 7, wherein the ROCK inhibitor is selected from the list consisting of HA-100, H-1152, and Y-27632.

9. The method of claim 2, wherein the method comprises culturing the cells in one or more of steps 1) through 3) at an atmospheric pressure of about 5-20% oxygen.

10. The method of claim 2, wherein step (a) comprises differentiating the pluripotent cells into embryoid bodies (EBs).

11. The method of claim 2, wherein step (a) comprises culturing the pluripotent cells in a first media comprising at least one of FLT-3 ligand, stem cell factor (SCF), thrombopoietin (TPO), interleukin-3 (IL-3), and interleukin-6 (IL-6).

12. The method of claim 11, wherein the first media comprises stem cell factor.

13. The method of claim 11, wherein step (a) comprises culturing the pluripotent cells in a first media comprising at least two of FLT-3 ligand, stem cell factor, thrombopoietin (TPO), interleukin-3 (IL-3), and interleukin-6 (IL-6).

14. The method of claim 13, wherein step (a) comprises culturing the pluripotent cells in a media comprising FLT-3 ligand, stem cell factor, TPO, IL-3, and IL-6.

15. The method of claim 14, wherein FLT-3 ligand, stem cell factor, TPO, IL-3, and IL-6 are exogenously added and recombinant.

16. The method of claim 15, wherein the first media comprises about 10-100 ng/ml FL3, about 10-100 ng/ml stem cell factor, about 10-100 ng/ml TPO, about 10-100 ng/ml IL-3, and about 10-100 ng/ml IL-6 are exogenously added and recombinant.

17. The method of claim 2, wherein after step (a) a plurality of the pluripotent cells have been differentiated into either megakaryocytes or mast cells, wherein the mast cells are positive for CD117 and CD45, while being negative for CD34.

18. The method of claim 2, wherein the media further comprises interleukin-6 (IL-6).

19. The method of claim 18, where the media comprises about 10-100 ng/ml stem cell factor and about 10-100 ng/ml IL-6.

20. The method of claim 2, wherein the culturing of at least one of step (a) and/or step (b) are performed using serum-free media.

21. A method of preparing human mast cells by culturing human pluripotent cells in vitro comprising the steps of:
   a) culturing human pluripotent cells under conditions that promote differentiation of the cells into hematopoietic progenitor cells or megakaryocytes, to provide a first cell population comprising hematopoietic precursors or megakaryocytes; and
   b) culturing the first cell population under conditions that promote the differentiation into mast cells, to provide a second cell population comprising mast cells;
wherein the step (a) culturing step does not employ a co-culture with murine fetal liver-derived stromal cells as a feeder layer;
wherein the step (b) culturing step comprises culturing the cells in a media comprising stem cell factor;
wherein the method further comprises purifying mast cells using MACS or FACS.

22. The method of claim 21, wherein step (a) comprises culturing cells under conditions which favor differentiation of the pluripotent cells into hematopoietic cells, wherein the resulting hematopoietic cells are cultured under conditions which favor differentiation into mast cells.

23. A method of preparing human mast cells by culturing human pluripotent cells in vitro comprising the steps of:
   a) culturing human pluripotent cells under conditions that promote differentiation of the cells into hematopoietic progenitor cells or megakaryocytes, to provide a first cell population comprising hematopoietic precursors or megakaryocytes; and
   b) culturing the first cell population under conditions that promote the differentiation into mast cells, to provide a second cell population comprising mast cells;
wherein the step (a) culturing step does not employ a co-culture with murine fetal liver-derived stromal cells as a feeder layer;
wherein the step (b) culturing step comprises culturing the cells in a media comprising stem cell factor;
wherein step (a) comprises culturing cells under conditions which favor differentiation of the pluripotent cells into hematopoietic cells and subsequently culturing the hematopoietic cells under conditions which favor differentiation into megakaryocytes, wherein the resulting cells are cultured under conditions which favor differentiation into mast cells.

* * * * *